US006458597B1

(12) United States Patent
Andrien, Jr. et al.

(10) Patent No.: US 6,458,597 B1
(45) Date of Patent: *Oct. 1, 2002

(54) DIRECT FLOW INJECTION ANALYSIS NEBULIZATION ELECTROSPRAY AND APCI MASS SPECTROMETRY

(75) Inventors: Bruce A. Andrien, Jr., Guilford; J. Fred Banks, Old Saybrook; James Boyle, Madison, all of CT (US)

(73) Assignee: Analytica of Branford, Inc., Branford, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/532,724

(22) Filed: Mar. 22, 2000
(Under 37 CFR 1.47)

Related U.S. Application Data

(60) Provisional application No. 60/125,492, filed on Mar. 22, 1999.

(51) Int. Cl.[7] .............................. B01D 59/44; H01J 49/00

(52) U.S. Cl. ...................... 436/173; 250/281; 250/282; 250/285

(58) Field of Search ........................... 250/281, 282, 250/285; 436/173

(56) References Cited

U.S. PATENT DOCUMENTS

| | | | | |
|---|---|---|---|---|
| 4,842,701 A | * | 6/1989 | Smith et al. ............ | 250/281 X |
| 4,999,493 A | * | 3/1991 | Allen et al. ................. | 250/288 |
| 5,572,023 A | * | 11/1996 | Caprioli ...................... | 250/288 |
| 5,844,237 A | * | 12/1998 | Whitehouse et al. ....... | 250/288 |

OTHER PUBLICATIONS

K. L. Johnson et al, Rapid Commun. Mass Spec. 1997, 11, 939–942.*
T. Covey et al, Anal. Chem. 1983, 55, 2275–2280.*
A. P. Bruins J. Chromatog. 1991, 554, 39–46.*
S. Jackett et al, Rev. Sci. Instrum. 1994, 65, 591–596.*
R. Kostianen et al, Rapid Commun. Mass Spectrom. 1994, 8, 549–558.*
W. H. Cusworth, III et al, AT–PROCESS 1995, 1, 110–114.*
Q. Wu et al, Rapid Commun. Mass Spectrom. 1996, 10, 835–838.*
J. F. Banks, Jr. et al, Methods Enzym. 1996, 270, 486–519.*
S. Geromanos et al, Rapid Commun. Mass Spectrom. 1998, 12, 551–556.*
S. J. Lane et al, Rapid Commun. Mass Spectrom. 1998, 12, 947–954.*
R. E. Moore et al, Anal. Chem. 1998, 70, 4879–4884.*

* cited by examiner

Primary Examiner—Arlen Soderquist
(74) Attorney, Agent, or Firm—Levisohn, Lerner, Berger & Langsam, LLP

(57) ABSTRACT

A method and apparatus for Flow Injection Analysis (FIA) into Atmospheric Pressure Ion sources (API) including Electrospray (ES) and Atmospheric Pressure Chemical Ionization (APCI) sources whereby the sampling and spray needles are one and the same. The sampling and spray needle configured with an autoinjector apparatus or used in manual injection is introduced directly into a mating ES or APCI probe configured in an API source. Such a sampling and spray needle eliminates the need for injector valves, transfer lines or additional fluid delivery systems in FIA into API sources interfaced to mass spectrometers or other chemical analyzers. The use of a sampling and spray needle configuration reduces component costs, liquid dead volume, sample dilution effects, and minimizes cross contamination effects, solvent consumption and waste while increasing sample throughput.

127 Claims, 11 Drawing Sheets

US 6,458,597 B1

DIRECT FLOW INJECTION ANALYSIS NEBULIZATION ELECTROSPRAY AND APCI MASS SPECTROMETRY

RELATED APPLICATIONS

The present application claims all rights of priority to U.S. Provisional Application Ser. No. 60/125,492 filed Mar. 22, 1999, the contents of which are fully incorporated herein by reference.

FIELD OF THE INVENTION

The present invention relates to apparatus and methods in the field of mass spectrometry.

BACKGROUND OF THE INVENTION

Flow injection analysis (FIA) performed with an atmospheric pressure ion (API) source interfaced to a mass spectrometer (MS) is a common method for introducing sample into an API MS apparatus. Typically, API MS FIA is performed by connecting a sample injector valve in-line between a solvent or solution delivery system and an inlet probe to an API source. When the injector valve is switched to the load position, sample solution is loaded into the injector valve through an injector needle while the separate solvent delivery system provides liquid flow to the API source probe through a separate channel in the injector valve. The injector valve is then switched so that the loaded sample solution, usually contained in a tubing loop or channel, is connected to the solvent delivery channel and the sample solution flows into the API source through the API probe at a flow rate set by the solvent delivery system. The injector valve is generally connected to the API source probe with a transfer line or tube. The sample is introduced into the injector valve through an injector needle that is connected to a fluid reservoir or transfer line. The injector needle may be connected to a syringe for manual injection, a syringe configured in an autoinjector or transfer tube or line that is connected to a remote fluid delivery means configured in an autoinjector. In some commercially available autoinjectors, the injector needle is attached directly to a syringe. The syringe and injector needle are loaded, emptied and positioned by the autoinjector apparatus. The autoinjector moves the injector needle into a vial or container holding sample solution and loads a programmed volume of sample solution into the injector needle and attached syringe. The autoinjector apparatus then moves the syringe and injector needle position to the injector valve and loads the sample solution into the injector valve. To avoid sample carryover from one sample solution injection to the next, the injection needle inner bore and outer surface and the syringe inner volume may be washed or flushed between sample injections.

Other commercially available autoinjectors do not attach the injector needle directly to a syringe but instead connect the injector needle to a fluid transfer line or tube that is in turn connected to a syringe or fluid pump which may or may not translate with the injector needle position. Sample solutions are drawn into the injector needle and connected tubing and injected into the injector valve by activating the remote syringe or fluid delivery pump when the injector needle is appropriately positioned in a sample vial or the injector valve respectively. A number of apparatus and methods have been employed in commercial autoinjectors to flush or wash the outer and inner bore of injection needles and the connected tubing between sample injections. Typically, autoinjector needles are metal tubes with sufficient rigidity to push through the seal of an injector valve or sample vial top. The flow rate of sample solution pulled into or delivered from the injection needle is programmably controlled by the autoinjector syringe or positive displacement fluid flow pump. Autoinjectors can be programmed to inject sample solutions drawn from multiple sample vials or containers in an unattended sequence. Each sample loaded into the injector valve is subsequently injected or delivered to the API MS where a portion of the sample is ionized and mass to charge analysis. Alternatively, some or all sample solution transfer, injection and injector needle cleaning steps performed by an autoinjector can be performed manually as well with a handheld syringe or a syringe mounted on an syringe pump that is connected through a transfer line and an injection needle to the injector valve.

API MS performance can be reduced using conventional FIA configured with injector valves and transfer lines. MS signal resulting from ES and APCI source ionization is essentially sample concentration dependent. Dilution of the sample can occur in injector valves and transfer lines due to diffusion of sample solution into the mobile solvent, mixing connection points and in dead volumes and adsorption to the walls. Such dilution can result in reduced MS signal or tailing of injection peaks. Sample that has adsorbed to surfaces in the injector valve or liquid transfer lines can bleed off during subsequent sample injections. Such sample carry over can appear as added peaks or chemical noise in subsequent injections and may cause errors in trace component or quantitative MS analysis. The effects of the dead volumes from injection valves, connections and fluid deliver or transfer lines become increasingly pronounced as the liquid flow rate or sample concentration decreases. When the liquid flow rate is decreased, the sample transit time in the injector valve and transfer tubing increases for a given dead volume. Longer sample transit times allow increased sample diffusion into the solvent, diluting the sample. Higher liquid flow rates may require more total sample to be injected to accommodate slower MS data acquisition rates encountered with scanning mass spectrometers such as quadrupoles.

The Electrospray needle in some commercial ES sources is operated at kilovolt potentials during spraying. For such ES sources, a longer dielectric liquid transfer line of several inches is typically configured between the ground potential injector valve and the ES needle to allow a gradual drop in kilovolt potential through the sample solution. A high electric field gradient in the transfer tube is avoided to minimize sample heating, electrophoretic and electrolysis effects during FIA. Liquid transfer lines can be reduced in length when an ES source in configured with a grounded needle, however, even with grounded ES needles, the dead volume due to the transfer lines cannot be entirely eliminated. For API MS FIA applications where small amounts of sample are available for injection, sample dilution or losses due to injector valve, connector and transfer line dead volumes and surfaces may compromise the limit of detection. Sample handling techniques employed in conventional FIA apparatus and methods may be the primary limitation in achieving lower limits of detection in API MS FIA analysis.

The invention reduces or eliminates those elements configured and used in conventional FIA apparatus and methods that reduce API MS FIA performance. In one preferred embodiment of the invention, the injector needle and an ES source has been configured such that the sample solution can be sprayed directly from the injector needle tip. The injector needle tip is introduced into the ES source chamber through a probe that serves as a needle guide, seal, electrical connection and pneumatic nebulization second needle layer. The injector needle can be introduced into an APCI source through a similar probe apparatus serving as a needle guide, seal and pneumatic nebulization sprayer second tube layer. Multiple injection needles can be configured to spray in a multiplexed manner through one or more API probes to increase FIA sample throughput. The injector needle can be configured as a reusable or disposable tip. The liquid spray flow rate is set by the auto or manual injector sample injection flow rate. This flow rate can be set to optimize MS analysis and sample throughput. The invention reduces instrument cost by eliminating the need for an injector valve and controls, transfer lines and a separate solvent flow pump in API TOF FIA. The invention also minimizes solvent consumption and waste.

The invention allows increased sample throughput in API MS FIA applications by eliminating steps and the time associated with liquid transfer per injector needle. In one embodiment of the invention, multiple injector needles can be sequentially introduced into one API source probe or multiple injector needles can be introduced into an API source through multiple API source probes. T. Wang et. al., Proceedings of the 46$^{th}$ ASMS Conference on Mass Spectrometry and Allied Topics, 1034, 1998 have reported the configuration and use of multiple injector needles and valves to shorten analysis run time and increase sample throughput. Commercially available autoinjectors, such as the Gilson Multiprobe 215 liquid handler, have been configured with up to eight autoinjector needles dispensing to eight autoinjector valves which transfer sample through an additional selector valve to an API source. Fluid flow through such a system is provided by a separate liquid flow pump. The transfer lines have increased length from multiple injector valves when compared to the single injector valve configuration. The increased transfer and dead volumes from each injector valve through the transfer lines and the switching valve to the API source must be thoroughly flushed between injections. The speed of injections even with such a multiple injector valve configuration is still limited to some extent by the washing and flushing of the eight injector valves, transfer lines and switching valve. In one embodiment of the invention, multiple injector needles can be configured for introduction into one or more API probes without the need to add multiple injector valves, transfer lines, switching valves or an additional fluid flow pump. Increases in sample throughput can be achieved with the invention at a lower cost, when compared with commercially available systems, without a reduction in performance that is unavoidable in API MS FIA apparatus with higher dead volumes. In the invention internal flushing or cleaning is limited to the injector needle and the attached reservoir and external flushing is limited to the injector needle only to avoid cross talk or contamination sample carry over from one injection to another. Flushing or cleaning of valves or transfer lines is eliminated in FIA according to the invention.

SUMMARY OF THE INVENTION

The invention comprises a reusable or disposable injector needle configured in an autoinjector or a manual injector which serves as the means to remove a sample solution from a container and transport such solution to an API source wherein the injector needle, when introduced into the API source, serves as the spray needle to deliver sample directly into the API source chamber. Such fixed or disposable injector needle, when introduced into an API source, becomes the liquid introduction channel or tube in the nebulizer probe of an APCI source, the nebulizer apparatus of a pneumatically assisted Electrospray probe or an Electrospray tip in an unassisted ES ion source probe. Ions produced from samples introduced through such sprayers into an API source are subsequently directed into vacuum where they are mass to charge analyzed. Ions transported into vacuum from such API source apparatus may also be subject to mass to charge selection and/or fragmentation in MS/MS or MS/MS$^n$ analysis. An API source may be configured with multiple direct injection needles and/or probes for introducing samples at an increased rate into an API source. Autoinjectors may be configured with multiple injector needles configured for direct delivery of sample into an API source through one or more probes. Such multiple needle autoinjectors may deliver samples in a sequential or multiplexed manner to such single or multiple direct injection API source ports or probes to maximize sample throughput. In one embodiment of the invention, a reusable or disposable sampling and spray injection needle may be packed with material, such as C18 coated beads, to aid in desalting, sample cleanup or the separation of sample compounds in solution during the sample pickup, delivery and spray steps. Different solvent composition layers can be pulled sequentially into such packed sampling and spray needles with attached reservoirs prior to sample pickup. The sample can then be sprayed into an API source from such a loaded injection needle using solvent gradients to aid in sample desalting, additional cleanup or sample compound separation during spraying.

Washing or flushing of a packed or open disposable injection needle, according to the invention, is not required between injections allowing an increase in sample throughput. In one embodiment of the invention, sample solution may be drawn up into a packed or open disposable injection needle. The injection needle is subsequently introduced into the API source and sample solution is sprayed from the injection needle tip with or without a solvent gradient to elute sample from any packed material. Alternately, a sample solution can be loaded into a non-disposable or reusable needle and the needle is then inserted into and forms a seal with a packed disposable injection needle. The packed injection needle is then introduced into an API source and the sample solution and any solvent gradient flows from the non-disposable needle through the packed disposable needle. The resulting solvent and sample solution is sprayed from the disposable needle tip into an API source. The packing material in the disposable tip serves to desalt or further clean the sample solution as well as to provide some sample component separation due to solvent gradient flow, if desired. Depending on the requirements of a specific analytical application, packing material may be replaced by filter media according to the invention to aid in sample cleanup with a minimum of dead volume.

The invention eliminates the need for sample injector valves or transfer lines into an API source, reducing sample dilution, loss and contamination due to sample handing and transfer. When a reusable needle is configured in the invention, the needle inner bore and outer surface can be washed in between each sample delivery and spraying step to reduce or eliminate, chemical noise, cross talk or carry over from one sample to the next. The use of disposable needles, configured according to the invention, eliminates sample to sample cross talk or contamination without a wash step between sample injections into the API source. Faster cycle times or more rapid sample injection throughput can be achieved by eliminating wash steps. Alternatively, a wash step can be run for one or more reusable injection needles while sample delivery and spraying is occurring with another injection needle or needles. The invention reduces apparatus costs, sample losses, sample contamination, and sample handling and minimizes solvent consumption and waste while increasing sample throughput in flow injection analysis with Atmospheric pressure ion sources. A direct injection needle apparatus may be configured with other API inlets in the same API source chamber as a means to increase analytical flexibility within one API source apparatus. Ions produced from the API source may be analyzed by apparatus other than MS including but not limited to ion mobility analyzers.

DETAILED DESCRIPTION OF THE INVENTION AND THE PREFERRED EMBODIMENTS

Figure 1:
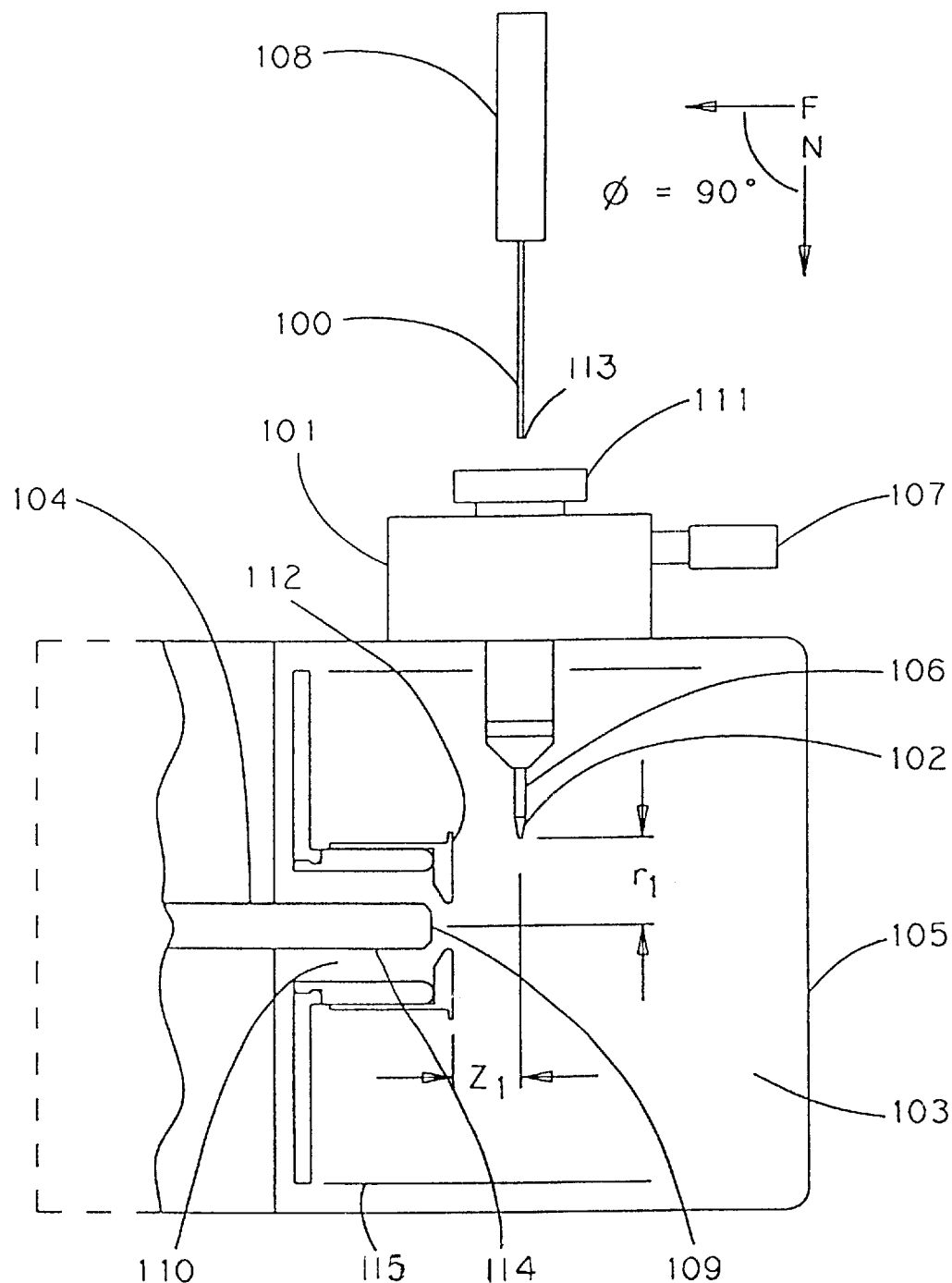
FIG. 1 is a diagram of a sampling and spray injection needle that is introduced into an ES source through an ES probe assembly whose axis is configured at an angle orthogonal to the axis of the vacuum entrance orifice.

The apparatus and methods used for flow injection analysis typically include an injector valve, transfer lines, fluid line connections, an addition fluid delivery pump, a sprayer probe with internal volume for ES and APCI sources and a switching valve when multiple injector valves are configured. Each of these elements adds to the dead volume or mixing volume encountered when delivering a sample solution into an API source in flow injection analysis. Added dead or mixing volumes can cause sample dilution due to diffusion or mixing of the sample with solvent during sample solution flow into an API source. Sample can adsorb to the walls of the valve, transfer line and probe transfer tube. Dilution of sample and loss of sample to the inner surfaces of the flow pathway results in reduced ion signal and analytical sensitivity. As liquid flow rates are reduced the sample solution spends more time in the transfer dead volumes. Increased transfer time results in increased sample dilution and loss to transfer surfaces. Adsorbed sample can bleed off valve, transfer line, connector and probe surfaces in subsequent injections, contributing chemical noise and interference peaks to acquired mass spectrum. Chemical noise or interference peaks due to contamination from prior injected sample can reduce the accuracy of quantitative measurements and compromise the limits of detection. Increased valve, connector, transfer line and probe surfaces require increased solvent flushing or cleaning time in between sample injections to minimize subsequent sample carry over or bleed. This required flushing increases solvent consumption and increases the time between injections. Increased cleaning time between injections decreases the number of samples that can be injected in a given time period, reducing sample throughput.

The invention allows rapid flow injection analysis over a wide range of liquid flow rates while minimizing solvent consumption and waste and eliminating all injector valves, fluid line connectors, transfer lines, probe liquid transfer tubes and additional liquid flow delivery system apparatus. Sample dilution or adsorption losses and solvent consumption are minimized with the invention and apparatus costs are reduced by elimination of components. Sample carry over or cross talk can be minimized with washing of reusable injection needles or eliminated with disposable or removable injection needles configured according to the invention. The invention comprises the configuration and use of an injector needle to draw up sample solution from a sample vial or container into the injector needle and attached solvent reservoir, transfer of the sample solution to an API source probe, passing of the injector needle through the API source probe channel and spraying of the sample solution from the tip of the injector needle into an API source. Ions are produced from the sprayed solution in the API source and are directed into vacuum where they are mass to charge analyzed. Alternatively, the ion population produced in the API source can be mass selected and fragmented in MS/MS or MS/MS$^n$ analysis. API sources may include but are not limited to ES, APCI or Inductively Coupled Plasma (OCP) ion sources. Mass to charge analysis can be conducted by any type of mass spectrometer including but not limited to quadrupoles, triple quadrupoles, Time-Of-Flight, three dimensional ion traps, Fourier Transform Mass Spectrometers (FTMS) or magnetic sector mass spectrometers.

Figure 2:
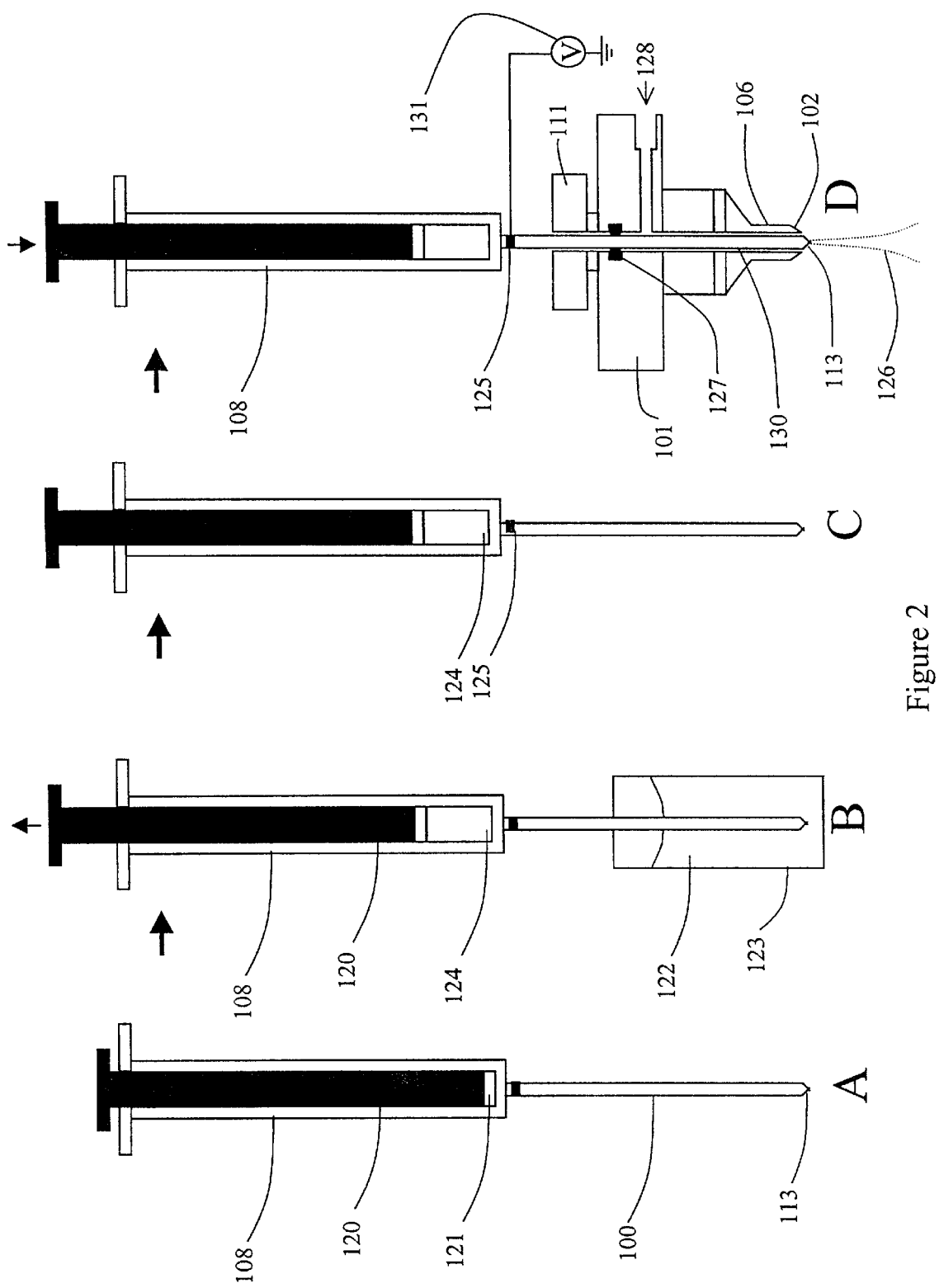
FIG. 2 is a diagram of the progression of sample loading and spraying with a reusable injection needle attached to a syringe reservoir in FIA according to the invention.

One embodiment of the invention is diagrammed in FIGS. 1 and 2 in which reusable injection needle 100 connected to syringe solvent reservoir 108 is configured to serve as an Electrospray needle in ES source 105. FIG. 2 is a diagram of the uptake of a sample solution from a sample vial or container, transfer of said sample solution to an ES source probe and the spraying of such sample solution into the ES source chamber using the same injector needle with attached solvent reservoir. Referring to FIG. 2, reusable injector needle 100 and attached syringe 108 are used to draw up sample solution 122 from sample vial or container 123 in diagrams A and B. In diagram A, syringe plunger 120 with plunger seal 121 is located in the full forward position in syringe 108. The inside bore of syringe 108 and injector needle 100 have been flushed with solvent to remove any previously injected sample. The outside surface of injector needle 100 has also been rinsed with solvent to remove any previously injected sample. With plunger 120 moved to the full forward position, cleaned injector needle 100 with tip 113 is inserted into sample solution 122 in sample vial or container 123. Plunger 120 is retracted or moved in the reverse direction to pull sample solution from sample vial 123 through the bore of injector needle 100 and into syringe volume 124 as diagrammed in FIG. 2B. Syringe 108 loaded with sample solution is moved from the sample vial position as shown in diagram C to a position where injection needle 100 is in-line with bore 130 of ES probe assembly 101 as shown in FIG. 1. Injector needle 100 is then moved through bore 130 of ES probe assembly 101 passing through entrance port 111, seal 127, tube 106 and tip 102. Electrical connection with electrically conductive injector needle 100 and ground or voltage supply 131 is made through contact 125 attached to injector needle 100.

Kilovolt electrical potentials are applied to cylindrical lens 115, nosepiece 112 and the capillary entrance lens 114 in ES source 105 when the injection needle and ES probe assembly 101 are operated at ground or zero electrical potential. Nebulization gas 128 is introduced through gas connection 107 and flows through the annulus described by the inner bore of tube 106 and the outer surface of injector needle 100 exiting at tip 102. Plunger 120 is moved forward causing sample solution to exit the syringe at injector needle tip 113. The sample solution is Electrosprayed with pneumatic nebulization assist from tip 113 due to the local electrical field gradient at tip 113 and the exiting nebulizing gas 128. Spray 126 comprises charged liquid droplets that evaporate as they move through ES chamber 103. A portion of the evaporating charged liquid droplets are directed by the electric field to move against counter current drying gas flow 110 toward capillary entrance orifice 109. Ions are released from such evaporating charged droplets and are directed into vacuum through capillary 104. Ions entering vacuum are subsequently mass to charge analyzed with a mass spectrometer. Details of the counter current drying gas 110 and capillary 104 configuration and function in API sources in described in U.S. Pat. Nos. 4,531,056 and 4,542,293 respectively and incorporated herein by reference. The liquid flow rate of spray 126 is controlled by the forward movement rate of syringe plunger 120. The filling, emptying and positioning of syringe 108 with injector needle 100 may be manually controlled or mechanically controlled as part of a programmable autoinjector or automated sample handling system to achieve API MS FIA.

Commercially available autoinjectors such as the Leap HTS PAL system are configured with syringes for the uptake, movement and injection of samples into injector valves. The syringes and attached injector needles are typically mounted to a programmable x-y-z position translator arm. Under pre-programmed control, sample solution is removed from a selected sample vial or vials, the loaded injector needle is moved to a position directly in-line with the bore of an ES probe assembly and the injector needle is introduced through the bore of the ES probe assembly in an ES source as diagrammed in FIGS. 1 and 2. Some commercially available autoinjectors are configured with multiple syringes. FIA sample throughput can be increased according to the invention when such multiple syringe autoinjectors are used. Such a multiple syringe autoinjector configuration can be operated whereby one syringe is spraying sample solution into ES source 105 while a second syringe is being flushed and cleaned prior to loading the next sample solution to be sprayed into the second injector needle and syringe. The syringes can be partially or completely filled with sample solution for each FIA run. The fill and spray liquid flow rates are determined by the syringe size used and the plunger movement rate as programmed in the autoinjector. Commercially available autoinjectors are configured to flush the internal bore of the syringe and injection needle and wash the injection needle external surface.

In an alternative embodiment to the invention, injector needle 100 is connected to a fluid transfer tube that may also serve as a sample solution reservoir instead of syringe 108. A fluid pump is connected to the opposite end of the fluid transfer tube controlling the sample solution flow into and out of injector needle 100. In such an embodiment, the fluid pump may or may not translate with the injector needle. Commercially available autoinjectors like the Hewlett Packard 1100 are configured with an injector needle connected to a tube made of peek, stainless steel or other material and the sample solution is loaded in the reverse flow direction through the injector needle and into such tube prior to injection of the sample solution in the forward flow direction through the injector needle tip. The sample solution volume removed from the sample vials and flow rate of the sample solution loading and spraying can be programmably controlled in commercially available autoinjectors configured with transfer tubing connected to the injector needle. Other commercially available autoinjectors are configured with a variations of injector needle and attached solution reservoir designs. Autoinjectors can be custom designed or modified to accommodate the translation and orientation of loaded injector needles into ES probe assembly bore 130. Such autoinjectors require an injector needle with sufficient rigidity to penetrate the septa of a sample vial and to push past seal 127 in ES probe assembly 101. Sample solution 122 is removed from sample vial 123 with reverse flow through injector needle 100 and held in solution reservoir 124. Loaded injector needle 100 is moved from sample vial 123, translated to ES source probe 101 and slid through bore 130 with tip 113 location programmably positioned inside, even with or slightly past tip 102 depending on the application and spraying conditions desired. Sample solution is then sprayed from tip 113 with or without pneumatic nebulization assist into ES chamber 103. A portion of the ions that are produced in ES source 105 are directed into vacuum where they are mass to charge analyzed. Variations of autoinjector designs may be configured which include the apparatus and methods of the invention. In the embodiment of the invention diagrammed in FIGS. 1 and 2, injector needle 100 and syringe 108 are configured as the only sample solution transport and delivery means. In this embodiment of the invention, sample cross contamination from one FIA sample to the next is restricted to injector needle needle 100 and syringe or storage reservoir 108. Consequently, internal flushing of injector needle 100 and syringe or storage reservoir 108 and external flushing of injector needle 100 minimizes or eliminates cross sample contamination in FIA. Injection needle and solution reservoir cleaning or flushing apparatus and programmable methods are available on most commercial autoinjectors.

As shown in the embodiment of the invention diagrammed in FIG. 1, the centerline of ES probe assembly 101 is oriented orthogonal to the bore of capillary 104. The position of probe tip 102 is located a distance $r_1$ from the capillary centerline and a distance $Z_1$ from the face of nosepiece 112. Injector needle 100 and ES probe assembly 101 can be operated at ground potential during Electrospraying when an ES source is configured with dielectric capillary tube 104. The potential of an ion being swept through the bore of dielectric capillary tube 104 into vacuum is described in U.S. Pat. No. 4,542,293. In alternative embodiments of the invention, the dielectric capillary can be replaced with a nozzle or conductive (metal) capillary and ES sources can be configured with or without heated counter current drying gas 110. When conductive capillaries or orifices are configured in ES source 105, injector needle 100 and ES probe tip 102 will be operated at high electrical potential relative to counterelectrodes 115, 112 and 114. Power supply 131 can be connected to injector needle 100 at contact 125 and to ES probe assembly 101 to apply the required high electrical potential, typically 3,000 to 6,000 volts during Electrospray operation. The Electrospray chamber 103 may be configured shorter in length and smaller in diameter due to the reduced flow rate range and total solution volume sprayed in FIA applications.

Figure 3:
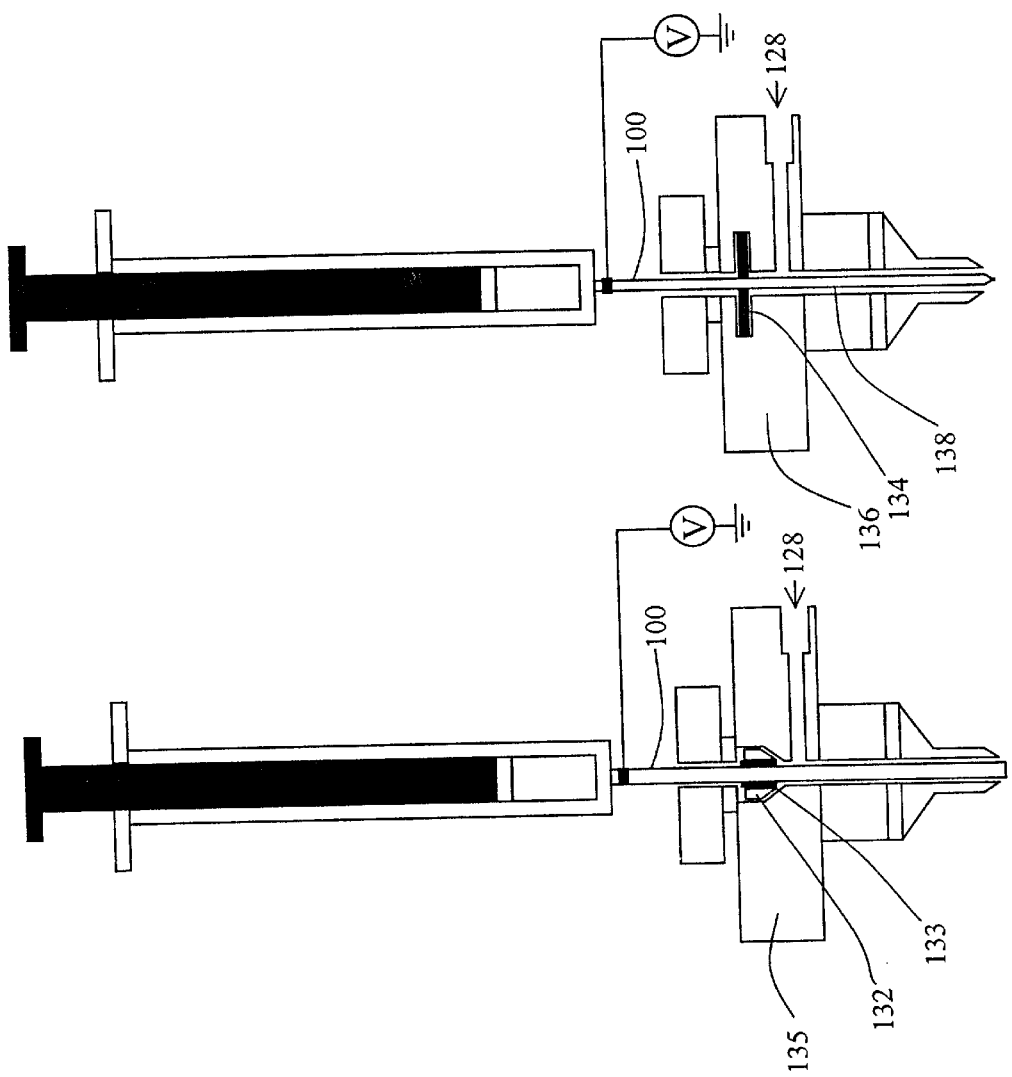
FIG. 3 includes two diagrams of reusable injector needles inserted into API probe assemblies with two different gas seals. The reusable injector needles are configured with syringes.

ES probe assembly 101 may be integrated into the walls of Electrospray chamber 103 or may be configured to penetrate through the wall of ES chamber 103. ES probe assembly 101 may be configured with alternative seals from that shown as seal 127 in FIG. 2D. Seal 127 in FIG. 2 may be replaced by ferrule 132 and seal 133 of ES probe assembly 135 or by septum seal 134 in ES probe assembly 136 as diagrammed in FIG. 3. Seals 127, 132 and 136 prevent nebulizer gas flow from exiting through entrance port 111 during Electrospraying with pneumatic nebulization assist. O-ring seal 127 may not close when injector needle 100 is removed from ES probe assembly 101. If nebulizing gas flow remains on when injector needle 100 has been removed, gas can flow out port 111 as well as through tip 102. Flushing nebulizer gas flow through ES probe assembly 101 during the time period between each sample solution spraying may be desirable to evaporate any solvent deposited in bore 130 when injector needle 100 is removed. Alternatively, nebulizing gas flow and even ES electrical potentials may be turned off when injector needle 100 is removed from ES probe assembly 101. Nebulizing gas and ES electrical potentials can be turned on when injector needle 100 is inserted into ES probe assembly 101. Commercial autoinjectors can be programmed to delay the dispensing of liquid from injector needle 100 for a period of time after injector needle 100 is inserted into ES probe assembly 101. This programmed delay allows the MS data acquisition system time to start, the nebulizing gas flow to stabilize, and the ES lens voltages to stabilize before the sample solution is Electrosprayed. Autoinjectors can also be programmed to dispense the sample at variable flow rates to optimize FIA performance. Ferrule 132 with seal 133 captured in ES probe assembly 135 of FIG. 3 may be configured to provide adequate gas sealing while imposing minimum resistance when inserting or removing injector needle 100. Septum seal 134 mounted in ES probe assembly 136 reseals when injector needle 100 is removed. Additional force may be required to reinsert injector needle 100 into bore 138 of ES probe assembly 136 when compared with the force required to insert injector needle 100 through seals 127 and 133. With alternative seals 133 or 136, nebulizer gas and ES electrical potentials can remain on at all times during FIA injection or they may be turned on only when injection needle 100 is inserted into an ES probe assembly. Turning off nebulizing gas flow 128 reduces gas consumption between each sample FIA.

Figure 4:
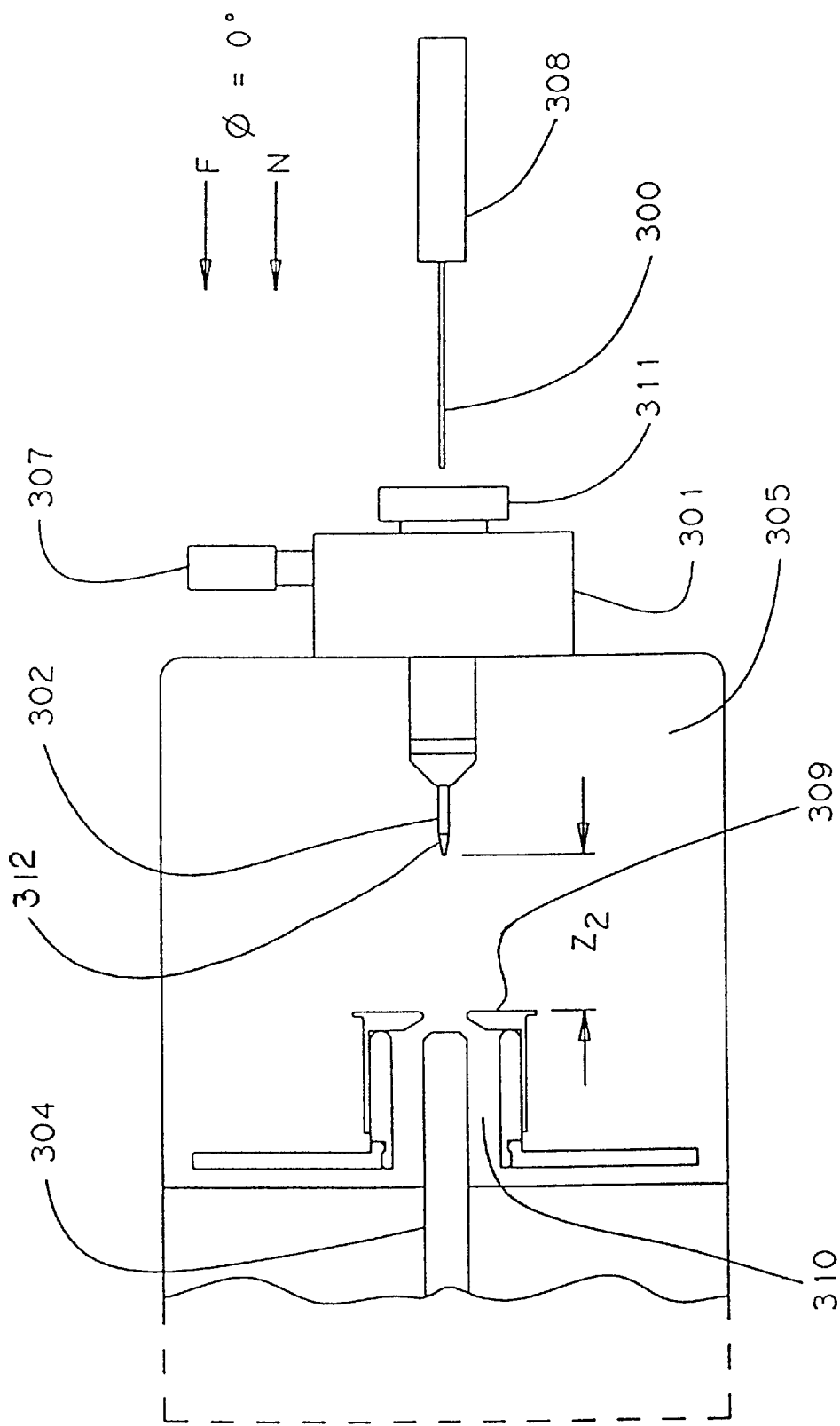
FIG. 4 is a diagram of a sampling and spray injection needle that is introduced into an ES source through an ES probe assembly whose axis is configured at an angle substantially the same as the axis to the vacuum entrance orifice.

Bore 130 of ES probe assembly 101 as diagrammed in FIG. 1 is positioned orthogonal to the bore of capillary 104. Commercially available ES sources include off axis and on axis ES probes with the angles of ES probe assembly centerlines ranging from zero to ninety degrees. U.S. Pat. No. 5,495,108 even describes ES probe positions with angles greater than 90 degrees. FIG. 4 shows a diagram of an embodiment of the invention in which the bore of ES probe assembly 301 is positioned on the same axis as the bore of capillary 304. The distance from ES probe tip 312 to nosepiece 309 is set at $Z_2$ in FIG. 4. The value for $Z_2$ ranges typically from 0.5 to 2 cm for ES flow rates ranging from 0.2 to 200 ul/min. ES source chamber 305 is configured with heated drying gas flow 310. ES probe assembly 301 is configured with inlet port 311, nebulizer gas port 307 and exit end 302 with tip 312. Injector needle 300 with attached reservoir 308 is inserted into ES probe assembly 305 as described in FIGS. 1 and 2 for the orthogonal ES probe embodiment. Higher sensitivity can be achieved for lower solution flow rates using on-axis ES probes compared with off axis probes. ES probe assemblies 101 and/or 301 can be oriented at any angle relative to the capillary bore axis. Multiple ES probe assemblies configured according to the invention can be mounted in the same ES chamber. ES probes configured according to the invention can be mounted with standard ES probes in the same ES source. Multiple ES and APCI probe assemblies configured in an API source are described in U.S. patent application Ser. No. 60/076,118 and incorporated herein by reference. Autoinjectors can be configured to position injector needles in the orientation required for insertion into ES probe assemblies configured according to the invention that are oriented at various angles in an ES chamber.

Figure 5:
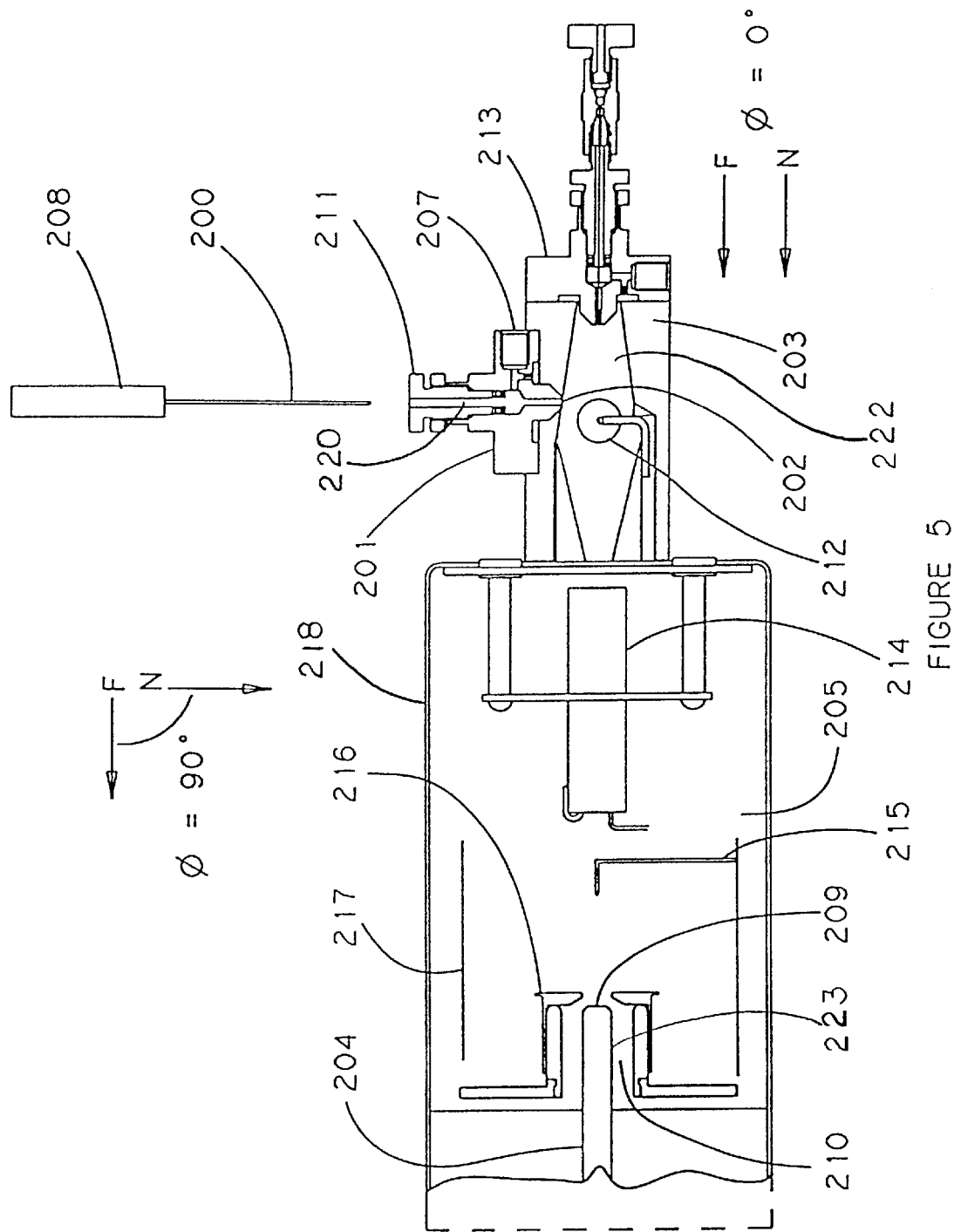
FIG. 5 is a diagram of a sampling and spray injection needle that is introduced into an APCI source through an APCI pneumatic nebulizer probe whose axis is configured at an angle orthogonal to the axis of the vacuum entrance orifice.

An alternative embodiment to the invention is diagrammed in FIG. 5 wherein injector needle 200 attached to reservoir 208 is configured to deliver sample solution through APCI nebulizer probe assembly 201. APCI source assembly 218 comprises two APCI inlet probe assemblies 201 and 213, droplet separator ball 212 in droplet transfer assembly 203, vaporizer heater 214, corona discharge needle 215 nosepiece 216, capillary 204, heated counter current gas 210 and cylindrical lens 217 in APCI chamber 205. Droplet separator ball 212 may or may not be included depending on the liquid flow rates being sprayed from API probes 201 and/or 213. Bore 220 of APCI nebulizer probe assembly 201 is oriented orthogonal to the APCI source centerline defined by the extension of the capillary orifice 209 centerline. The centerline of a second APCI nebulizer probe 213 which connects to a liquid transfer line, is positioned along the APCI source centerline. Sample solutions delivered through injector needle 200 and APCI probe assembly 213 are sprayed into chamber 222 before being swept through vaporizer 214. Sample solutions may be sprayed simultaneously or sequentially from APCI nebulizer probe assemblies 201 and 213. Sprayed liquid droplets from APCI probe assembly 201 or 213 evaporate as they pass through vaporizer heater 214. Kilovolt electrical potentials are applied to corona discharge needle 215 to form a corona discharge near the exit end of vaporizer heater 214. Sample bearing vapor is ionized as it passed through the corona discharge region near the tip of needle 215. A portion of the ions formed in the corona discharge region are directed against counter current gas flow 210 toward capillary orifice 209 by the electric fields formed from the electrical potentials applied to cylindrical lens 217 and needle 215, nosepiece 216 and capillary entrance lens 223. Ions are swept into vacuum through the bore of capillary 204 where they are mass to charge analyzed.

Figure 6:
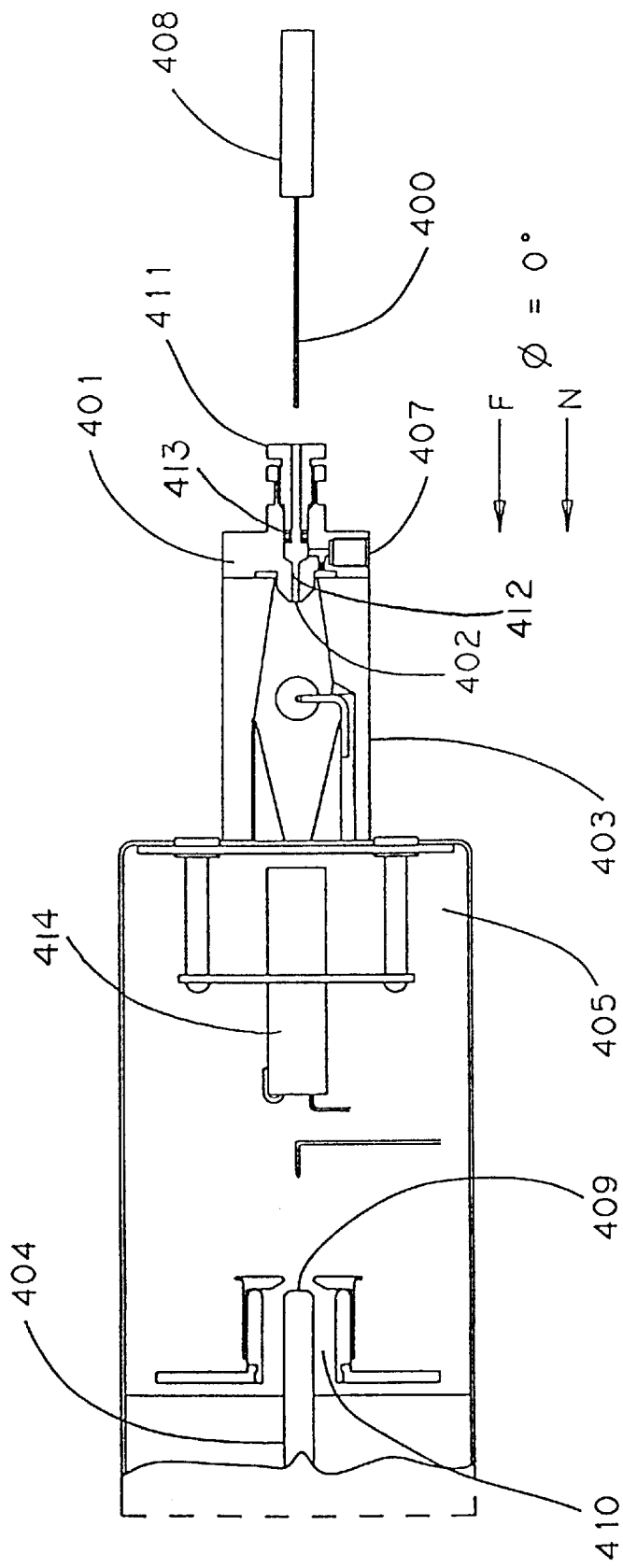
FIG. 6 is a diagram of a sampling and spray needle that is introduced into an APCI source through an APCI pneumatic nebulizer probe assembly whose axis is configured substantially the aligned with the axis of the orifice into vacuum.

In an alternative embodiment of the invention, FIG. 6 shows a diagram of APCI nebulizer probe 401 configured similar to APCI probe 201. Injector needle 400 attached to solution reservoir 408 can be slid through adjustable needle port 411, seal 413 and bore 412 of APCI nebulizer probe assembly 401. Nebulizer gas flow enters port 407 and flows between the inner diameter of bore 412 and the outer diameter of inserted injector needle 400. The tip of the inserted injector needle 400 is positioned relative to exit orifice 202 and 402 of APCI probe assemblies 201 or 401 respectively to optimize the nebulization efficiency of the liquid spray. The tip of injector needle 400 may be positioned slightly inside, even with or extended beyond exit orifice 202 or 402 depending on liquid and nebulizer gas flow rates. Sample solution sprayed from injector needle 400 passes through the droplet transfer region 403, through vaporizer heater 414 and into APCI chamber 405. Ions formed from the vaporized sample solution in the corona discharge region are directed against counter current gas flow 410 into orifice 409 of capillary 404 by the electric fields in APCI source chamber 405. Ions entering capillary orifice 409 are swept into vacuum through the bore to capillary 404 where they are mass to charge analyzed with a mass spectrometer.

The sequence of sample solution pick up and transfer to an API probe shown in FIG. 2 can be applied to injector needles 200 and 400 and APCI nebulizer probe assemblies 201 and 401. As in the Electrospray ion source embodiment, an APCI source can be operated in flow injection analysis mode using apparatus and methods according to the invention. Injector valves, transfer tubing, fluid line connections, probe liquid transfer tubing and additional fluid flow pumps can be eliminated when an injector needle and sample solution reservoir is configured and operated according to the invention in APCI MS FIA. Alternative seals may be configured in APCI probe assemblies 201 or 401 as diagrammed in FIG. 3 for ES probe assemblies 135 and 136. Bore 220 of APCI nebulizer probe assembly 201 may be oriented at any angle relative to the APCI source centerline. Multiple APCI nebulizer probes configured according to the invention may be mounted to droplet transfer assembly 203. As in the ES probe assembly embodiment of the invention, removable injector needle 200 or 400 may be attached to a syringe, a solution reservoir or a liquid transfer tube. Such a liquid transfer tube may be connected to a fluid flow pump to deliver sample solution through injector needle 200. Sample solution may be introduced in this manner to deliver a calibration solution into the ES or APCI sources sequentially or simultaneously with a second sample solution spray as is described in U.S. patent application Ser. No. 60/076, 118. The movement and positioning of injector needle 200 and attached solution reservoir 208 may be controlled manually or using a programmable mechanical apparatus such as an autoinjector. Autoinjectors can be configured to insert injector needle 208 into bore 220 of APCI probe assembly 201 at any angle required by the APCI source probe geometry. The total sample solution volume loaded and the liquid flow rates passing through injector needle 200 can be programmably controlled by an autoinjector apparatus. Multiple solution samples can be run sequentially in an ES and/or APCI source delivered from an autoinjector containing multiple sample vials from which sample solution can be loaded into an injector needle configured according to the invention.

It is obvious to one skilled in the art that variations of embodiments of the invention may include but are not limited to combinations of:

1. The ES or APCI probe assembly centerline to vacuum orifice centerline angles (f) may range from 0° to 180°;
2. ES or APCI probe assembly tip locations ($r_1, z_1,$) where $r_i$ may equal any distance, and $z_i$ may equal any distance within an ES chamber;
3. An API source capillary or orifice mounted in a position with its centerline ranging from horizontal to vertical;
4. The ES or APCI probe assembly can be combined with other ES probe types or APCI probes in the same API source as described in U.S. patent application Ser. No. 60/076,118;
5. The ES probe assembly may include pneumatic assisted Electrospray nebulization, ultrasonic assisted Electrospray nebulization or other nebulizer type or may be configured for unassisted Electrospray operation;
6. Electrospray probe may include two, three or more layer construction for use with or without additional liquid layer flow;
7. Multiple injector needles directed to one ES or APCI probe assembly or multiple injector needles directed to multiple ES or APCI probe assemblies; and
8. Multiple ES or APCI probe assemblies configured according to the invention and mounted in one API source apparatus.

Figure 7:
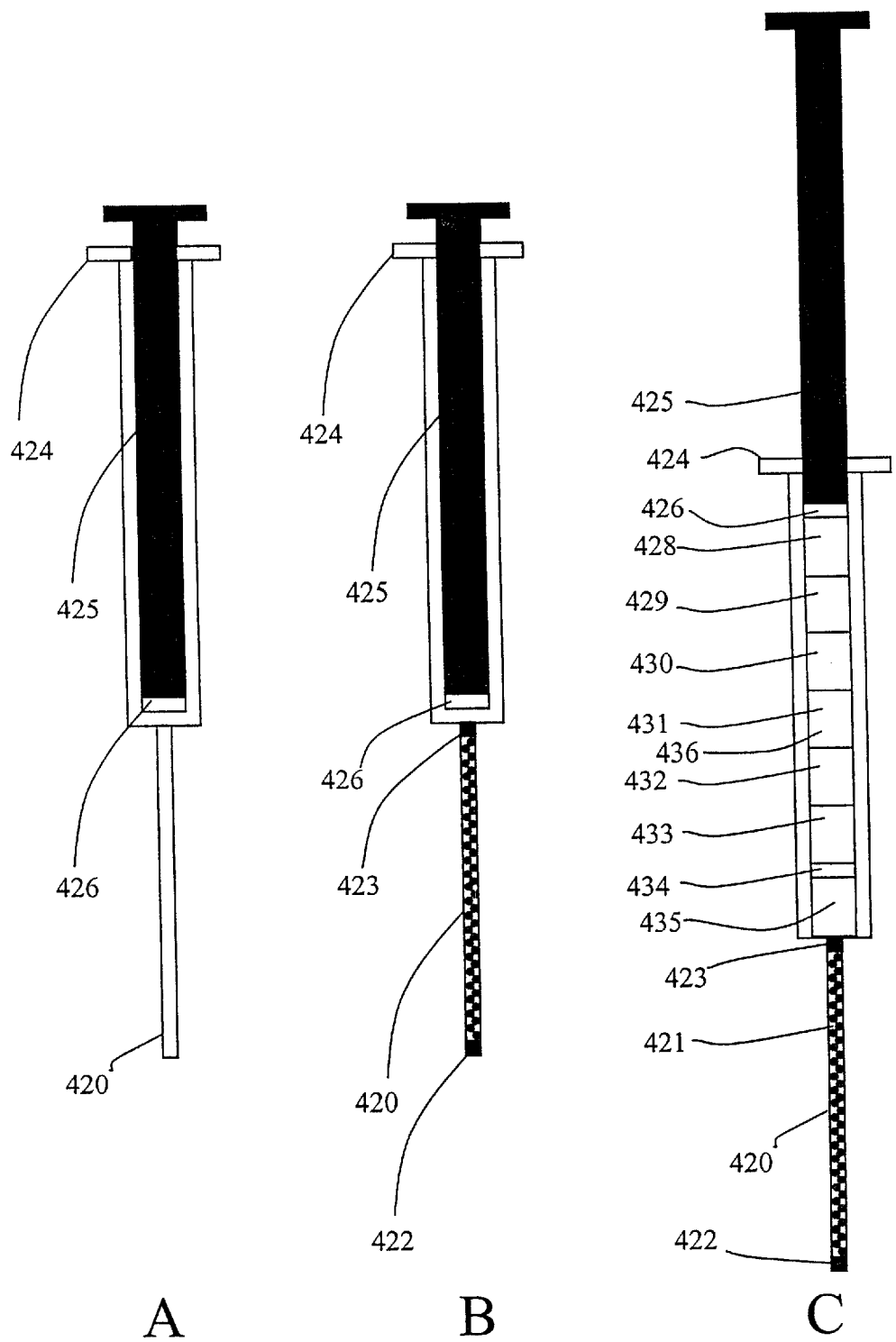
FIG. 7 is a diagram of a reusable injector needle configured with a syringe wherein the injector needle is filled with material to remove contaminants and separate sample components during FIA. Operation with solvent gradients in the syringe is illustrated.

An alternative embodiment of the reusable injector needle is shown in FIG. 7, wherein the internal bore of injector needle 420 is filled with packing material 421. Packing material 421 may comprise but is not limited to coated beads similar to those used in liquid chromatography columns or filter material. Frits 422 and 423 are configured at each end of the bore of injector needle 420 to retain packing material 421 during loading and delivery of sample solution through injector needle 420. FIG. 7A shows an external view of injector needle 420 attached to syringe 424 shown in cross section with plunger 425 and plunger seal 426 located in the full forward or empty position. FIG. 7B is a diagram of the cross section of packed injector needle 420 and syringe 424 prior to loading solvent and sample solution. The inclusion of packing material in injector needle 420 allows desalting and other sample cleanup as well as separation of components in the sample solution during API MS FIA. As sample solution is loaded from the sample vial, it passes through the packing material in injector needle 420. As an example, when FIA of peptides is performed, the packing material may be selected to be C18 coated beads. This C18 packing material is similar to the media packed in high pressure liquid chromatography columns that are used to conduct gradient separations of peptides. A partial sample component gradient separation can be achieved in FIA when the sample solution is delivered to an API source in through the packed injector needle 420 connected to a syringe loaded with a solvent gradient as shown in FIG. 7C.

Referring to FIG. 7C, syringe 424 with injector needle 420 is loaded with a series of solutions of different compositions 428 through 433 from sequentially from different containers to form a solvent gradient along the length of syringe reservoir 436. For example the composition of solution volume 428 may be 10% water and 90% acetonitrile with 0.05% TFA, solution volume 429, 30% water and 70% acetonitrile with 0.05% TFA to solution volume 433 which may be 90% water and 10% acetonitrile with 0.05% TFA. A solvent gradient is formed in syringe reservoir 436 from loading partial syringe volumes consecutively from a series of vials containing solution compositions ranging, in this example from 10% to 90% acetonitrile with 0.05% TFA. To divide the solvent gradient from the sample solution, air bubble volume 434 can be drawn into syringe 424 before loading sample solution volume 435. The sample solution containing a high percentage of water passes through the C18 media packed in the bore of injector needle 420 during loading. Salts and other contaminants pass through injector needle 420 into internal volume 436 of syringe 424 during loading of the sample solution while the peptide sample components of interest adsorb or stick to available sites on the C18 media in injector needle 420. When syringe 424 is loaded, it is moved and aligned with the bore of an API probe assembly and the injector needle is introduced through the API probe bore according to the invention as diagrammed in FIGS. 1 and 2 above. As syringe plunger 425 is moved forward, sample solution solvents, salts and contaminants contained in volume 435 are sprayed into the API source chamber while the peptide sample components remain adsorbed to packing material 421. Air bubble 434 and solvent gradient volume 433 through 428 pass through injector needle 420 as syringe 424 is emptied during ES or APCI MS FIA. As solvent volumes 433 through 428 pass through injector needle media 421, the adsorbed peptides will release from the C18 packing material with increasing organic content of the solvent solution. Some peptide component separation may occur as syringe 424 is emptied because different peptides may release from the C18 packing material at different organic solvent concentrations. Peptides spraying from packed injector needle 420 into an API source may be separated from salts or other contaminants contained in the original sample solution using this method. Some degree of chromatographic separation may also be achieved using this method during API MS flow injection analysis, improving the quality of acquired MS data. Flushing or cleaning between sample runs is limited to flushing packed injector needle 420 and the inner bore of syringe 424 and washing the outside surface of injector needle 420.

In alternative embodiments of the invention, a fluid transfer line or other solution reservoir may replace syringe 424 in FIG. 7. The loading, emptying and positioning of packed injector needle 420 with syringe 424 may be controlled manually or mechanically with programmable control. Syringe 420 configured with packed injector needle 420 may be mounted in an autoinjector which also contains several sample vials required to conduct the method described above. Packing material may extend into a solution reservoir in alternative embodiments of the invention. U.S. Pat. No. 5,572,023 describes the filling of fixed position Electrospray needles with chromatography packing material. In the apparatus described in U.S. Pat. No. 5,572,023, the packed Electrospray needle is connected to sample injector valves, transfer lines and multiple solvent pumps for conducting sample desalting of gradient separations in a single liquid flow direction. Sample cleanup and chromatographic separation in FIA can be achieved with the apparatus configured according to the invention without injector valves, liquid transfer lines or additional liquid flow pumps.

According to the invention, solution flow moves through the injector needle in the reverse direction during loading and in the forward direction during spraying. The loading of solvents and/or sample solution through the injector needle packing material may be aided by pressurizing the solution vials or containers.

The sample solution can alternatively be loaded without including bubble 434 if it is desirable to have a continuous liquid column when loading or spraying. A continuous liquid column provides increased tensile strength when pulling sample solution from a vial through packing material. When desalting is desired without chromatographic separation, a two part solvent front may be preloaded in syringe 424 instead of a number of different organic concentrations. In a stepwise manner, the first high percentage aqueous solvent volume will flush out salts and other contaminants through injector needle 420 while spraying and the second high percentage organic solvent volume passing through packing material 421 will release the adsorbed peptide components simultaneously during API source spraying. Injector needle 420 may be packed with filter media instead of chromatography packing material to remove contaminants from the sample solution prior to sample injection into the API source.

Figure 8:
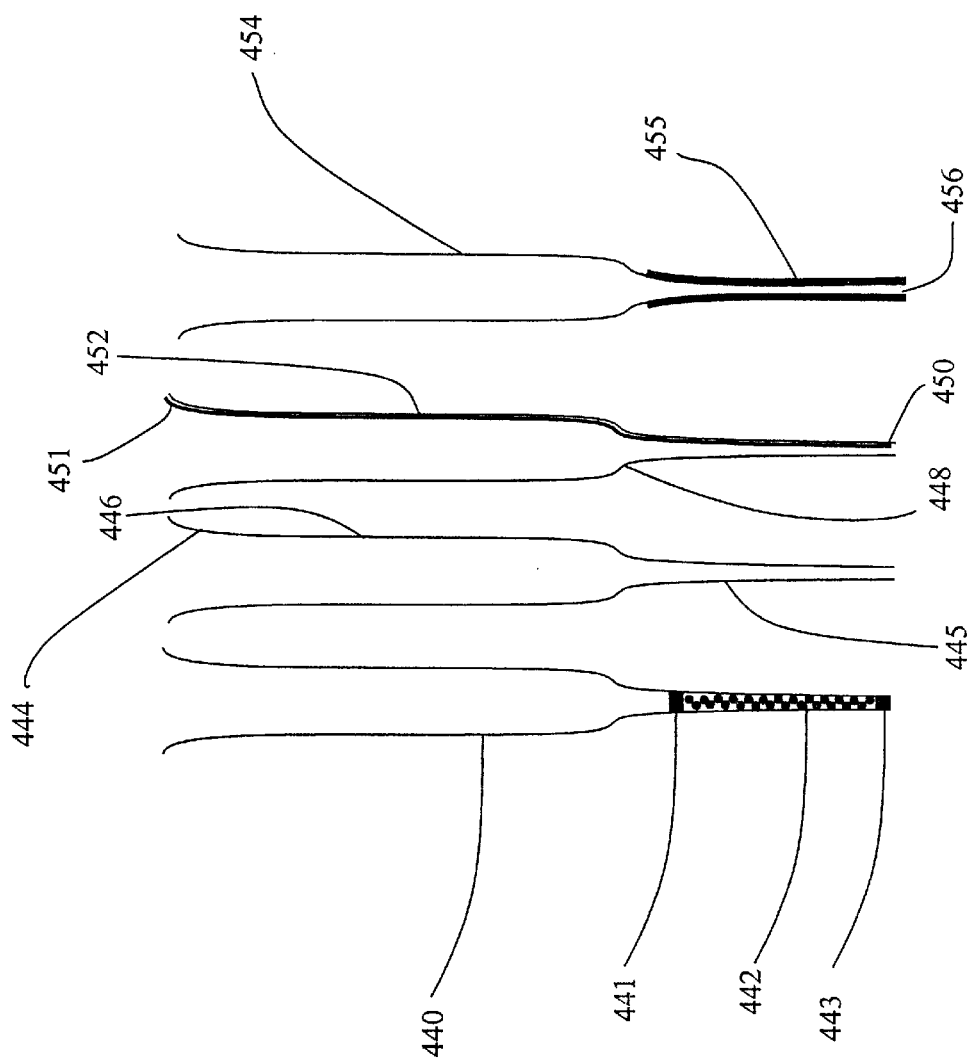
FIG. 8 is a diagram of removable injector needles configured with and without conductive elements attached and configured with and without filled tips.

In an alternative embodiment of the invention, the reusable injection needle is replaced by a removable or disposable injection needle. The removable injection needle may be comprised of a dielectric material such as molded plastic, a combination of dielectric and conductive material or entirely of conductive material. FIG. 8 is a diagram of four embodiments of removable or disposable injector needles configured according to the invention. Removable injector needle 444 is fabricated from dielectric material such as molded polyethylene. Removable injector needle 444 comprises the narrower needle portion 445 and the larger diameter upper portion 446. A portion of the removable injector needle inner volume may be filled with media such as filter or chromatography packing material. Such packing material can be used to remove contaminants from the sample solution or separate sample components as described for the reusable needle embodiment. Removable injector needle 440 in FIG. 8 is shown with packing material 442 filling the narrower needle portion of removable injector needle 440. In the embodiment shown, packing material is prevented from moving out of the bore of removable injector needle 440 by frits 441 an 443. Dielectric removable injector needles 440 and 444 may be used to spray samples into APCI sources where the formation of charged liquid droplets is not required. A conductive tip is preferred for Electrospraying from a removable injector needle. Two alternative embodiments of removable injector needles 448 and 454 with conductive elements configured in each tip are diagrammed in FIG. 8. In one embodiment, conductive strip 452 beginning at tip 450 and extending to the opposite opening end 451 is molded into or attached to the inside surface of removable injector needle 448. Conductive strip 452 provides electrical contact with the sample solution at tip 450 and a contact point at end 451 during Electrospraying. An alternative means to provide an electrical contact with the Electrospraying solution is shown with removable injection needle 454. Conductive material 455 is attached to the external surface of removable injection needle 454 surrounding tip 456. Conductive material 455 serves to provide electrical contact between the solution spraying from tip 456 with an electrical conductor external to removable injector needle 454 during Electrospray operation.

Figure 9:
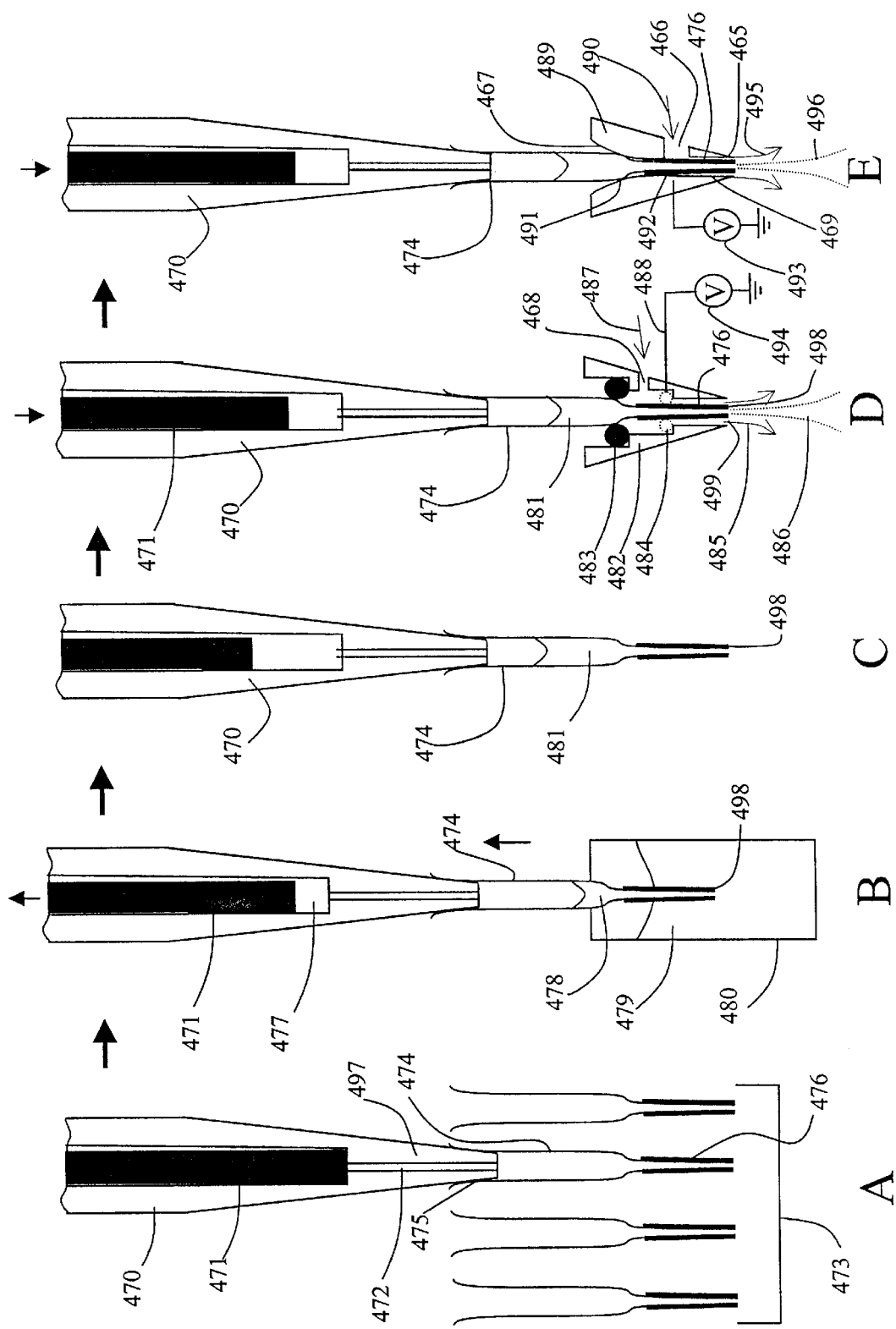
FIG. 9 is a diagram of the progression of sample loading and spraying with removable injector needles into an API source through an API source probe assembly according to the invention.

FIG. 9 diagrams embodiments of the invention wherein removable injection needles are used to load sample solution and conduct API MS flow injection analysis. Referring to FIG. 9, pipette device 470 is moved into position and inserted into removable injector needle 474 in set 473. Contact between the pipette device taper end 497 and removable injector needle 474 at point 475 provides a seal and sufficient friction to allow temporary attachment of removable injector needle 474 to taper end 497 of pipette device 470. Plunger 471 of pipette device 470 is located in its forward position in FIG. 9A when picking up removable injector needle 474. Channel 472 in pipette device 470 connects the plunger chamber volume with the internal volume of the attached injector needle 474. Removable injector needle 474, configured with electrical conductor 476 surrounding tip 498, is moved from set 473 to vial 480 containing sample solution 479 as shown in FIG. 9B. Plunger 471 is moved in the reverse direction to load sample solution 478 into removable injection needle 474 through the opening at tip 498. Volume 477 created by retracting plunger 471 determines the volume of sample solution loaded into removable injector needle 474. The desired sample solution volume 481 is loaded into removable injector tip 474, and if necessary for greater volume, into plunger volume 477. Pipette device 470 with loaded attached injector needle 474 are moved from container 480 to a position where tip 498 can be inserted into to the bore of API probe assembly 482 as shown in FIG. 9C and D. When removable injector needle 474 is fully inserted into API probe assembly 482, the outer diameter of removable injector needle 474 forms a gas seal with probe seal 483. Electrical contact to ground or power supply 494 is made to conductive material 476 through contact 484 and connection 488. Nebulizer gas flow 487 enters API probe assembly 482 through port 468 and exits at probe tip 499 flowing through the annulus between conductive material 476 and the bore of API probe 482. The forward movement of plunger 471 pushes sample solution 481 out through tip 498 creating ES or APCI spray 486.

An alternative embodiment of API probe assembly 489 is shown in FIG. 9E. A gas seal is formed by contact point 491 between the API probe assembly body and removable injector needle 474. Electrical contact is made directly between conductive material 476 and the conductive body of API probe assembly 489 due to the taper of tip 489 mating with API probe assembly inner bore 469. API probe assembly 489 may be grounded or connected to voltage supply 493 for ES sources where it is required that the ES probe be operated at kilovolt potentials. Nebulizer gas 490 enters API probe assembly 489 through port 466 and exits at API probe tip 465 where nebulizer gas flow 495 aids in forming spray 496 from sample solution in ES and APCI source operation. Typically, tip 498 of removable injection needle 474 has a small diameter and consequently is not sufficiently rigid to push through a seal or a septum. Entrance end 467 of API probe assembly 489 is tapered to guide the thin filament tube end 498 through inner bore 469. A manual injector or autoinjector may be configured with a separate rigid tube that is use to pierce a septum sealing a sample solution vial. The removable injection needle can then be passed through the rigid tube passing through the septum to load sample solution from the sample vial. After flow injection analysis is completed, pipette device 470 with attached injector needle 474 is withdrawn from API probe assembly 489 or 482. Removable injector needle 474 is detached from pipette device 470, a new removable injector needle is attached to pipette device 470 and the FIA cycle as diagrammed in FIG. 9 is repeated. No wash cycle is required when removable injector needles are used in flow injection analysis resulting in decreased cycle time per sample. Total sample throughput can be increased when using removable injector needles in FIA without any sample carryover or contamination from sample to sample.

Figure 10:
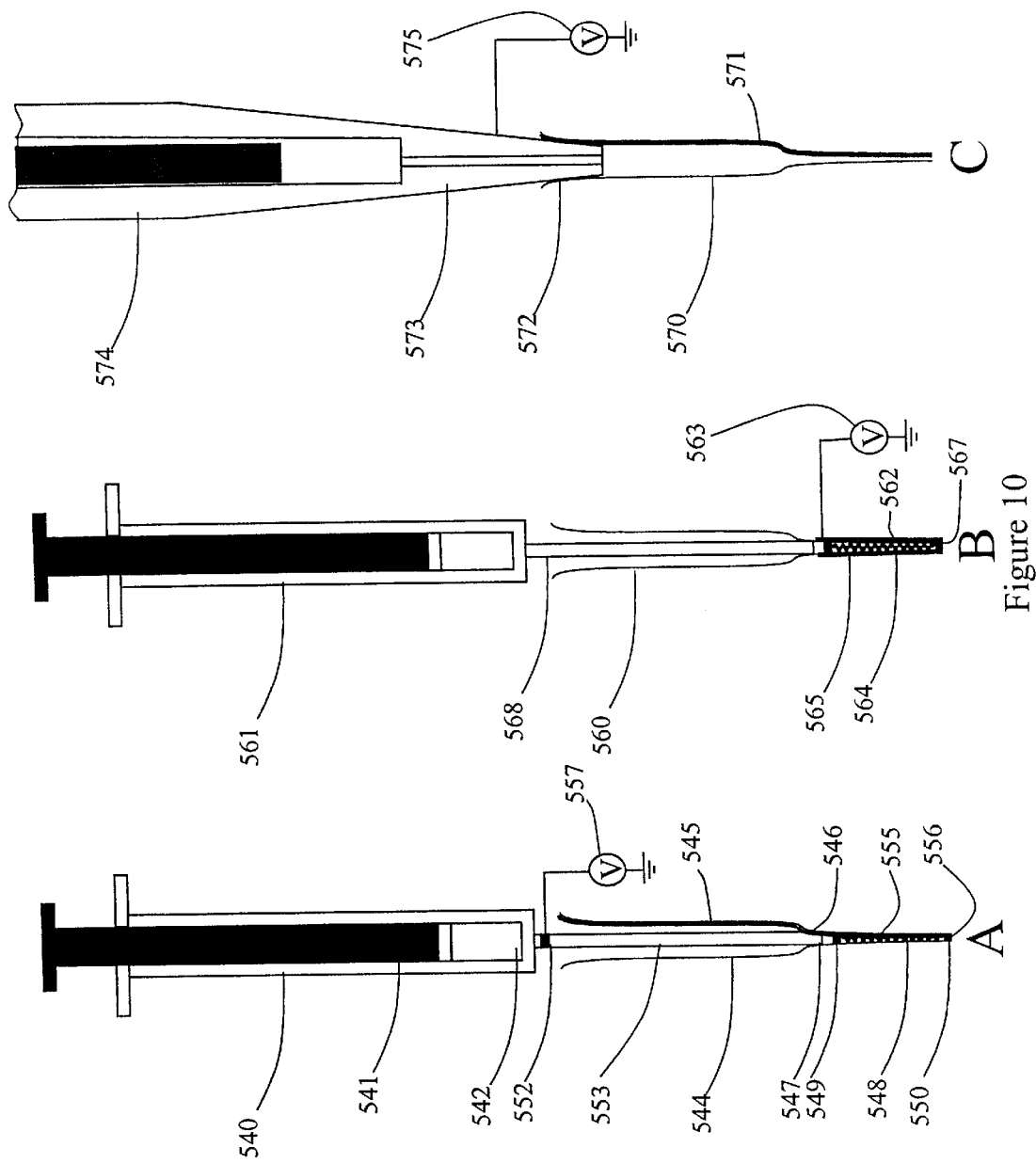
FIG. 10 is a diagram syringe and pipette devices attached to different configurations of removable injector needles.

Filling, emptying and positioning of pipette device 470 can be controlled manually or using programmable mechanical devices such as autoinjectors or automatic pipette controllers. Alternative embodiments of the invention can be configured to control the filling, emptying and positioning of removable injection needles as is diagrammed in FIG. 10. Referring to FIG. 10A, syringe 540 with attached needle 553 when inserted into removable injector needle 544 forms a seal a point 547 and electrical contact with inner conducting strip 551. Removable injector needle 544 is shown with tip end 555 filled with packing material 548 contained by frits 549 and 550. Electrical contact between ground or voltage supply 557 and tip 556 is made through conducting strip 545, needle 553 and electrical contact 552 when tip 556 is operated as an Electrospray tip. Reverse and forward movement of plunger 541 fills or empties reservoir 542 with sample solvent or sample solution respectively through removable injector needle 544 during API MS FIA. An alternative embodiment of the invention is shown in FIG. 10B. Removable injector needle 560 is configured with conductive material 565 coating the outer surface of packed tip 562. Electrical connection with tip 567 to ground or voltage supply 563 is made through contact between conductive material 565 and an API probe assembly as was diagrammed in FIG. 9. No direct electrical connection is made between tip 567 and syringe needle 568 or syringe 561 in the embodiment diagrammed in FIG. 10B eliminating any electrical connections between syringe 561 and a voltage supply or ground potential. An alternative embodiment of the invention is diagrammed in FIG. 10C wherein removable injector needle 570 with electrically conductive strip 571 makes an electrical connection to ground or voltage supply 575 through electrical contact with the conductive tapered portion 573 of pipette device 574. Variations and/or combinations of embodiments shown may be configured and used according to the invention to perform flow injection analysis with atmospheric pressure ion sources interfaced to mass spectrometers, ion mobility analyzers or other analytical devices.

Figure 11:
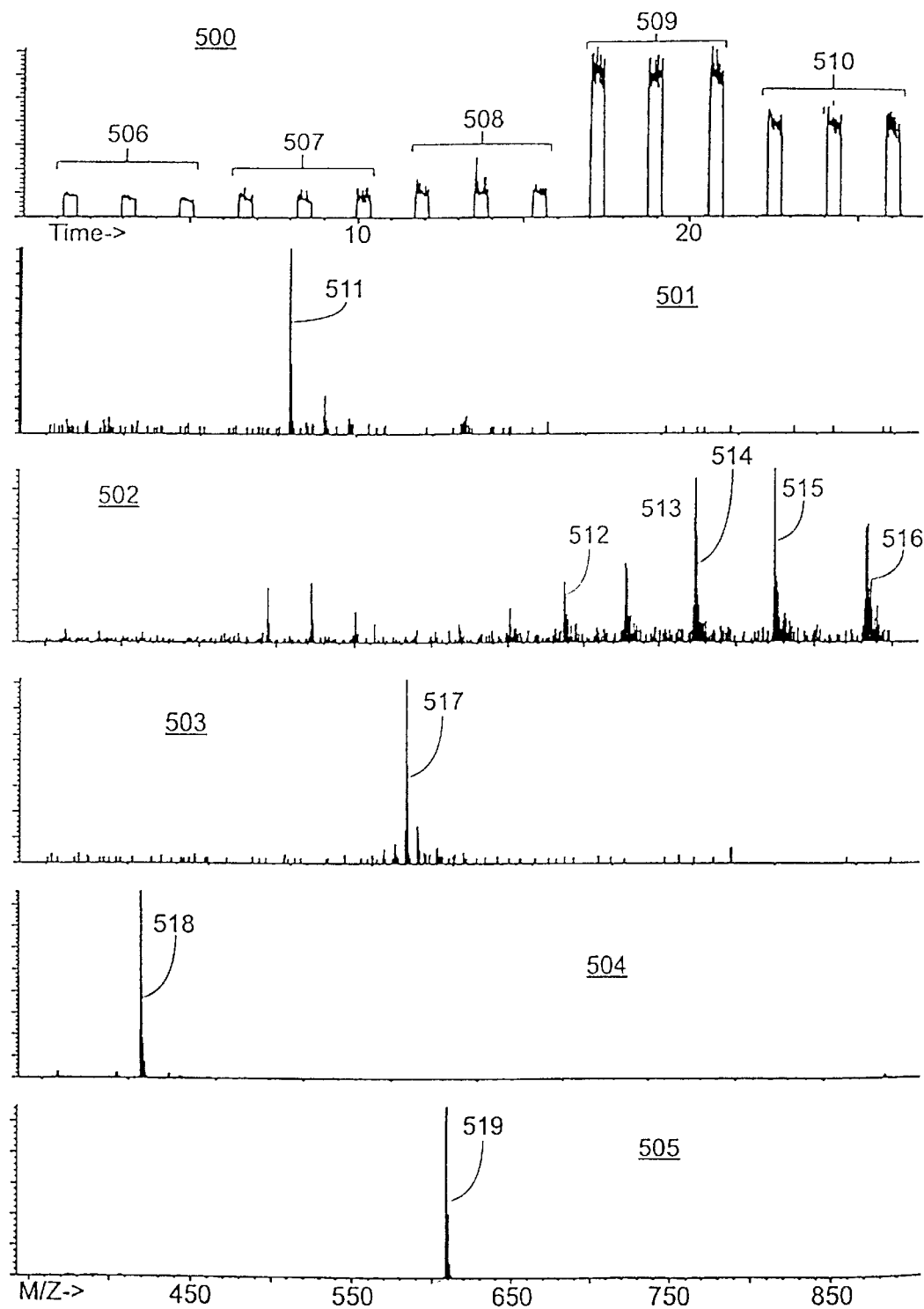
FIG. 11 includes a Total Ion Chromatogram and five representative mass spectra acquired in accordance with the invention by repeated injections of different samples using an autoinjector configured with a sampling and spray injector needle that is introduced into an ES source interfaced to a mass spectrometer.

FIG. 11 shows the results acquired from ES MS flow injection analysis using the embodiment of the invention diagrammed in FIGS. 1 and 2. FIG. 11 includes a total ion current (TIC) trace in curve 500 and five mass spectra 501–505 acquired by spraying sample solution into an Electrospray ion source configured as diagrammed in FIG. 1. A 100 ul syringe mounted in a Leap HTS PAL autoinjector was used to load and deliver sample solution to the ES probe assembly. The autoinjector flow rate when spraying the sample solution from the injector needle attached to the syringe was set at 200 ul/min for the data acquired in FIG. 11. Three injections each were made of five different samples as are shown in TIC trace 500 of FIG. 11. The first three TIC peaks 506 are of Tri-Tyrosine injected at a concentration of 50 pmole/$\mu$L. Mass spectrum 501 was acquired under one of the TIC peaks of 506. Mass spectrum 501 shows the singly charged protonated molecular ion peak 511 of Tri-Tyrosine peak which hs a measured mass to charge value of 508. Injections of 10 pmole/ul sample solutions of protein cytochrome-C form the second three TIC peaks 507 corresponding to injections four through six. Mass spectrum 502 of cytochrome-C was acquired under one of the TIC peaks in 507. Mass spectrum 502 shows peaks 512, 513, 514, 515, and 516 of multiply charged protonated molecular ions of cytochrome-C corresponding to mass to charge values 688, 728, 773, 825, and 884 respectfully. The third set of TIC peaks 508 were acquired by injecting sample solution containing 1 pmole/ul of gramicidin-S. Mass spectrum 503 acquired under one of these injection peaks 503, shows the doubly charged protonated molecular ion peak 517 of gramicidin-S. The fourth set of three TIC peaks 509 were acquired by injecting a sample solution containing 11 pmole/ul of Lincomycin. Mass spectrum 504 acquired under one of the TIC peaks 509, shows the singly charged protonated molecular ion peak 518 of Lincomycin with a measured mass to charge of 407. The last three TIC peaks 510 were acquired by sequentially injecting sample solutions containing 82 pmole/ul of reserpine. Mass spectrum 505 was acquired under one of the TIC peaks 510 and shows the singly charged protonated molecular ion peak 519 of reserpine which has a measured mass to charge value of 609. The data shown in FIG. 11 is an example of ES MS FIA acquired according to the invention with no injector valve, transfer lines, probe transfer volumes, tubing connectors or additional fluid flow pumps. No cross talk or sample carryover is observed in TIC trace 500 or acquired mass spectra 501–505.

Having described this invention with regard to specific embodiments, it is to be understood that the description is not meant as a limitation since further modifications and variations may be apparent or may suggest themselves. It is intended that the present application cover all such modifications and variations, including those as fall within the scope of the appended claims.

REFERENCES CITED

The following references are referred to above, the disclosures of which are hereby fully incorporated herein by reference:

U.S. Patent Documents:

| | | |
|---|---|---|
| 5,495,108 | Feb. 27, 1996 | Apffel, James; Werlich, Mark; Bertach, James. |
| Provisional | Sept. 12, 1997, | Adrien Jr., Bruce A, Sansone, Michael A, Whitehouse, Craig M. |
| 4,542,293 | Sept. 17, 1985, | Fenn, John B, Yamashita, Masamichi, Whitehouse, Craig. |
| 5,572,023 | Nov. 5, 1996, | Caprioli, Richard. |
| 4,531,056 | July 23, 1985 | Labowski, Michael, Fenn John, B., Yamashita, Masamichi |

PUBLICATIONS

T. Wang, L. Zeng, T. Strader, L. Burton, and Daniel B. Kassel, Proceedings of the $46^{th}$ ASMS Conference on Mass Spectrometry, 1034, 1998.

We claim:

1. An apparatus for producing ions from chemical species in solution comprising:
   a) a needle for withdrawing a sample bearing solution from a container, said needle configured to draw said sample bearing solution therein and spray said sample bearing solution therefrom;
   b) an ion source operated a substantially atmospheric pressure, a probe assembly in said ion source which produces ions from sample bearing solutions, said probe assembly having an opening for removably inserting of said needle, said needle and probe assembly configured to produce ions from chemical species in said sample solution as it is sprayed from the needle with the needle inserted into the opening of the probe assembly; and
   c) a vacuum region in fluid communication with said ion source for receiving said ions.

2. An apparatus according to claim 1, wherein said ion source is an Electrospray source.

3. An apparatus according to claim 2, wherein said Electrospray source has pneumatic assist means.

4. An apparatus according to claim 2, wherein said Electrospray source has ultrasonic assist means.

5. An apparatus according to claim 2, wherein said Electrospray source has nebulization assist means.

6. An apparatus according to claim 2, wherein said Electrospray source comprises two tube layers.

7. An apparatus according to claim 2, wherein said Electrospray source comprises three or more tube layers.

8. An apparatus according to claim 1, wherein said ion source is an Atmospheric Pressure Chemical Ionization source.

9. An apparatus according to claim 8, wherein said Atmospheric Pressure Chemical Ionization source has pneumatic assist means.

10. An apparatus according to claim 8, wherein said Atmospheric Pressure Chemical Ionization source has ultrasonic assist means.

11. An apparatus according to claim 8, wherein said Atmospheric Pressure Chemical Ionization source has nebulization assist means.

12. An apparatus according to claim 8, wherein said Atmospheric Pressure Chemical Ionization source comprises two tube layers.

13. An apparatus according to claim 8, wherein said Atmospheric Pressure Chemical Ionization source comprises three or more tube layers.

14. An apparatus according to claim 1, wherein said needle is a syringe.

15. An apparatus according to claim 1, wherein said needle is an injection needle and storage reservoir from an autoinjector.

16. An apparatus according to claim 15, wherein said injection needle is an injection needle with its needle filled with a liquid chromatography material for desalting of the sample.

17. An apparatus according to claim 15, wherein said injection needle is an injection needle with its needle filled with a liquid chromatography material and said storage reservoir is partially filled with a liquid chromatography material for desalting of the sample.

18. An apparatus according to claim 15, wherein said storage reservoir is partially filled with a liquid chromatography material for desalting of the sample.

19. An apparatus according to claim 15, wherein said injection needle is an injection needle with its needle filled with a liquid chromatography material for liquid chromatography separations.

20. An apparatus according to claim 15, wherein said injection needle is an injection needle filled with a liquid chromatography material and said storage reservoir is partially filled with a liquid chromatography material for liquid chromatography separations.

21. An apparatus according to claim 15, wherein said storage reservoir is partially filled with a liquid chromatography material for liquid chromatography separations.

22. An apparatus according to claim 15, wherein said injection needle is an injection needle having an inside surface along said needle, wherein said inside surface is coated with a liquid chromatography material for desalting of the sample.

23. An apparatus according to claim 15, wherein said injection needle is an injection needle having an inside surface along said needle, wherein said inside surface is coated with a liquid chromatography material and said storage reservoir is partially coated with a liquid chromatography material for desalting of the sample.

24. An apparatus according to claim 15, wherein said storage reservoir is partially coated with a liquid chromatography material for desalting of the sample.

25. An apparatus according to claim 15, wherein said injection needle is an injection needle having an inside surface along said needle, wherein said inside surface is coated with a liquid chromatography material for liquid chromatography separations.

26. An apparatus according to claim 15, wherein said injection needle is an injection needle having an inside surface along said needle, wherein said inside surface is coated with a liquid chromatography material and said storage reservoir is partially coated with a liquid chromatography material for liquid chromatography separations.

27. An apparatus according to claim 15, wherein said storage reservoir is partially coated with a liquid chromatography material for liquid chromatography separations.

28. An apparatus according to claim 15, wherein said injection needle is an injection needle having an inside surface along said needle, wherein said inside surface is coated with a liquid chromatography material and said storage reservoir is partially coated with a liquid chromatography material for liquid chromatography separations.

29. An apparatus as set forth in claim 1 wherein said needle comprises an electrically conductive material to form an electrode.

30. An apparatus for producing ions from a chemical species in solution comprising:
   a) a needle for withdrawing a sample bearing solution from a container, said needle configured to draw said sample bearing solution therein and spray said sample bearing solution therefrom;
   b) an ion source operated a substantially atmospheric pressure, a probe assembly in said ion source which produces ions from sample bearing solutions, said probe assembly having an opening for removably inserting of said needle, said needle and probe assembly configured to produce ions from chemical species in said sample solution as it is sprayed from the needle with the needle inserted into the opening of the probe assembly; and
   c) means for mass analyzing said ions from the ion source.

31. An apparatus according to claim 30, wherein said means for mass analyzing said ions comprises a Time-Of-Flight mass spectrometer.

32. An apparatus according to claim 30, wherein said means for mass analyzing said ions comprises a Quadrupole mass spectrometer.

33. An apparatus according to claim 30, wherein said means for mass analyzing said ions comprises an Ion Trap mass spectrometer.

34. An apparatus according to claim 30, wherein said means for mass analyzing said ions comprises a Fourier Transform mass spectrometer.

35. An apparatus according to claim 30, wherein said means for mass analyzing said ions comprises a magnetic sector mass spectrometer.

36. An apparatus according to claim 30, wherein said means for mass analyzing said ions comprises a hybrid mass spectrometer.

37. An apparatus according to claim 30, wherein said ion source is an Electrospray source.

38. An apparatus according to claim 37, wherein said Electrospray source has pneumatic assist means.

39. An apparatus according to claim 37, wherein said Electrospray source has ultrasonic assist means.

40. An apparatus according to claim 37, wherein said Electrospray source has nebulization assist means.

41. An apparatus according to claim 37, wherein said Electrospray source comprises two tube layers.

42. An apparatus according to claim 37, wherein said Electrospray source comprises three or more tube layers.

43. An apparatus according to claim 30, wherein said ion source is an Atmospheric Pressure Chemical Ionization source.

44. An apparatus according to claim 43, wherein said Atmospheric Pressure Chemical Ionization source has pneumatic assist means.

45. An apparatus according to claim 43, wherein said Atmospheric Pressure Chemical Ionization source has ultrasonic assist means.

46. An apparatus according to claim 43, wherein said Atmospheric Pressure Chemical Ionization source has nebulization assist means.

47. An apparatus according to claim 43, wherein said Atmospheric Pressure Chemical Ionization source comprises two tube layers.

48. An apparatus according to claim 43, wherein said Atmospheric Pressure Chemical Ionization source comprises three or more tube layers.

49. An apparatus according to claim 30, wherein said needle is a syringe.

50. An apparatus according to claim 30, wherein said needle is the injection needle and storage reservoir from an autoinjector.

51. An apparatus according to claim 50, wherein said injection needle is filled with a liquid chromatography material for desalting of the sample.

52. An apparatus according to claim 50, wherein said injection needle is filled with a liquid chromatography material and said storage reservoir is partially filled with a liquid chromatography material for desalting of the sample.

53. An apparatus according to claim 50, wherein said storage reservoir is partially filled with a liquid chromatography material for desalting of the sample.

54. An apparatus according to claim 50, wherein said injection needle is filled with a liquid chromatography material for liquid chromatography separations.

55. An apparatus according to claim 50, wherein said injection needle is filled with a liquid chromatography material and said storage reservoir is partially filled with a liquid chromatography material for liquid chromatography separations.

56. An apparatus according to claim 50, wherein said storage reservoir is partially filled with a liquid chromatography material for liquid chromatography separations.

57. An apparatus according to claim 50, wherein said injection needle is an injection needle having an inside surface along said needle, wherein said inside surface is coated with a liquid chromatography material for desalting of the sample.

58. An apparatus according to claim 50, wherein said injection needle is an injection needle having an inside surface along said needle, wherein said inside surface is coated with an liquid chromatography material and said storage reservoir is partially coated with a liquid chromatography material for desalting of the sample.

59. An apparatus according to claim 50, wherein said storage reservoir is partially coated with a liquid chromatography material for desalting of the sample.

60. An apparatus according to claim 50, wherein said injection needle is an injection needle having an inside surface along said needle, wherein said inside surface is coated with a liquid chromatography material for liquid chromatography separations.

61. An apparatus according to claim 50, wherein said injection needle is an injection needle having an inside surface along said needle, wherein said inside surface is coated with a liquid chromatography material and said storage reservoir is partially coated with a liquid chromatography material for liquid chromatography separations.

62. An apparatus according to claim 50, wherein said storage reservoir is partially coated with a liquid chromatography material for liquid chromatography separations.

63. An apparatus as set forth in claim 30 wherein said needle comprises an electrically conductive material to form an electrode.

64. A method for producing ions from chemical species in a solution comprising:
   a) withdrawing a sample bearing solution from a vial with a needle,
   b) removably inserting the sample bearing solution containing needle into an opening in a probe assembly of an ion source, said ion source operated at atmospheric pressure to produce ions from sample bearing solutions,
   c) centering the needle containing sample bearing solution within said probe assembly,
   d) spraying said sample bearing solution from said needle, said probe assembly and needle operating to produce ions as the sample bearing solution is sprayed, and
   f) delivering said ions into a vacuum region.

65. A method according to claim 64, wherein said ion source is an Electrospray source.

66. A method according to claim 65, wherein said Electrospray source has pneumatic assist means.

67. A method according to claim 65, wherein said Electrospray source has ultrasonic assist means.

68. A method according to claim 65, wherein said Electrospray source has nebulization assist means.

69. A method according to claim 65, wherein said Electrospray source comprises two tube layers.

70. A method according to claim 65, wherein said Electrospray source comprises three or more tube layers.

71. A method according to claim 64, wherein said ion source is an Atmospheric Pressure Chemical Ionization source.

72. A method according to claim 71, wherein said Atmospheric Pressure Chemical Ionization source has pneumatic assist means.

73. A method according to claim 71, wherein said Atmospheric Pressure Chemical Ionization source has ultrasonic assist means.

74. A method according to claim 71, wherein said Atmospheric Pressure Chemical Ionization source has nebulization assist means.

75. A method according to claim 71, wherein said Atmospheric Pressure Chemical Ionization source comprises two tube layers.

76. A method according to claim 71, wherein said Atmospheric Pressure Chemical Ionization source comprises three or more tube layers.

77. A method according to claim 64, wherein said needle is a syringe.

78. A method according to claim 64, wherein said needle is an injection needle and storage reservoir from an autoinjector.

79. A method according to claim 78, wherein said injection needle is an injection needle with its needle filled with a liquid chromatography material for desalting of the sample.

80. A method according to claim 78, wherein said injection needle is an injection needle with its needle filled with a liquid chromatography material and said storage reservoir is partially filled with a liquid chromatography material for desalting of the sample.

81. A method according to claim 78, wherein said storage reservoir is partially filled with a liquid chromatography material for desalting of the sample.

82. A method according to claim 78, wherein said injection needle is an injection needle filled with a liquid chromatography material for liquid chromatography separations.

83. A method according to claim 78, wherein said injection needle is an injection needle filled with a liquid chromatography material and said storage reservoir is partially filled with a liquid chromatography material for liquid chromatography separations.

84. A method according to claim 78, wherein said storage reservoir is partially filled with a liquid chromatography material for liquid chromatography separations.

85. A method according to claim 78, wherein said injection needle is an injection needle having an inside surface along said needle, wherein said inside surface is coated with a liquid chromatography material for desalting of the sample.

86. A method according to claim 78, wherein said injection needle is an injection needle having an inside surface along said needle, wherein said inside surface is coated with a liquid chromatography material and said storage reservoir is partially coated with a liquid chromatography material for desalting of the sample.

87. A method according to claim 78, wherein said storage reservoir is partially coated with a liquid chromatography material for desalting of the sample.

88. A method according to claim 78, wherein said injection needle is an injection needle having an inside surface along said needle, wherein said inside surface is coated with a liquid chromatography material for liquid chromatography separations.

89. A method according to claim 78, wherein said injection needle is an injection needle having an inside surface along said needle, wherein said inside surface is coated with a liquid chromatography material and said storage reservoir is partially coated with a liquid chromatography material for liquid chromatography separations.

90. A method according to claim 78, wherein said storage reservoir is partially coated with a liquid chromatography material for liquid chromatography separations.

91. A method according to claim 78, wherein said injection needle is an injection needle having an inside surface along said needle, wherein said inside surface is coated or filled with a liquid chromatography material and said storage reservoir is partially coated or filed with a liquid chromatography material for liquid chromatography separations.

92. A method as set forth in claim 64 further comprising the step of creating an electrode of said needle containing said sample bearing solution.

93. A method for producing ions from chemical species in a solution comprising:
   a) withdrawing a sample bearing solution from a vial with a needle,
   b) removably inserting the sample bearing solution containing needle into an opening in a probe assembly of an ion source, said ion source operated at atmospheric pressure to produce ions from sample bearing solutions,
   c) centering the needle containing sample bearing solution within said probe assembly,
   d) spraying said sample bearing solution from said needle, said probe assembly and needle operating to produce ions as the sample bearing solution is sprayed, and f) mass analyzing said ions from the ion source.

94. A method according to claim 93, wherein said ions are mass analyzed in a Time-Of-Flight mass spectrometer.

95. A method according to claim 93, wherein said ions are mass analyzed in a Quadrupole mass spectrometer.

96. A method according to claim 93, wherein said ions are mass analyzed in an Ion Trap mass spectrometer.

97. A method according to claim 93, wherein said ions are mass analyzed in a Fourier Transform mass spectrometer.

98. A method according to claim 93, wherein said ions are mass analyzed in a magnetic sector mass spectrometer.

99. A method according to claim 93, wherein said ions are mass analyzed in a hybrid mass spectrometer.

100. A method according to claim 93, wherein said ion source is an Electrospray source.

101. A method according to claim 100, wherein said Electrospray source has pneumatic assist means.

102. A method according to claim 100, wherein said Electrospray source has ultrasonic assist means.

103. A method according to claim 100, wherein said Electrospray source has nebulization assist means.

104. A method according to claim 100, wherein said Electrospray source comprises two tube layers.

105. A method according to claim 100, wherein said Electrospray source comprises three or more tube layers.

106. A method according to claim 93, wherein said ion source is an Atmospheric Pressure Chemical Ionization source.

107. A method according to claim 106, wherein said Atmospheric Pressure Chemical Ionization source has pneumatic assist means.

108. A method according to claim 106, wherein said Atmospheric Pressure Chemical Ionization source has ultrasonic assist means.

109. A method according to claim 106, wherein said Atmospheric Pressure Chemical Ionization source has nebulization assist means.

110. A method according to claim 106, wherein said Atmospheric Pressure Chemical Ionization source, comprises two tube layers.

111. A method according to claim 106, wherein said Atmospheric Pressure Chemical Ionization source comprises three or more tube layers.

112. A method according to claim 93, wherein said needle is a syringe.

113. A method according to claim 93, wherein said needle is an injection needle and storage reservoir from an autoinjector.

114. A method according to claim 113, wherein said injection needle is filled with a liquid chromatography material for desalting of the sample.

115. A method according to claim 113, wherein said injection needle is filled with a liquid chromatography material and said storage reservoir is partially filled with a liquid chromatography material for desalting of the sample.

116. A method according to claim 113, wherein said storage reservoir is partially filled with a liquid chromatography material for desalting of the sample.

117. A method according to claim 113, wherein said injection needle is filled with a liquid chromatography material for liquid chromatography separations.

118. A method according to claim 113, wherein said injection needle is filled with a liquid chromatography material and said storage reservoir is partially filled with a liquid chromatography material for liquid chromatography separations.

119. A method according to claim 113, wherein said storage reservoir is partially filled with a liquid chromatography material for liquid chromatography separations.

120. A method according to claim 113, wherein said injection needle is an injection needle having an inside surface along said needle, wherein said inside surface is coated with a liquid chromatography material for desalting of the sample.

121. A method according to claim 113, wherein said injection needle is an injection needle having an inside surface along said needle, wherein said inside surface is coated with a liquid chromatography material and said storage reservoir is partial coated with a liquid chromatography material for desalting of the sample.

122. A method according to claim 113, wherein said storage reservoir is partially coated with a liquid chromatography material for desalting of the sample.

123. A method according to claim 113, wherein said injection needle is an injection needle having an inside surface along said needle, wherein said inside surface is coated with a liquid chromatography material for liquid chromatography separations.

124. A method according to claim 113, wherein said injection needle is an injection needle having an inside surface along said needle, wherein said inside surface is coated with a liquid chromatography material and said storage reservoir is partially coated with a liquid chromatography material for liquid chromatography separations.

125. A method according to claim 113, wherein said storage reservoir is partially coated with a liquid chromatography material for liquid chromatography separations.

126. A method according to claim 113, wherein said injection needle is an injection needle having an inside surface along said needle, wherein said inside surface is coated or filled with a liquid chromatography material and said storage reservoir is partially coated or filled with a liquid chromatography material for liquid chromatography separations.

127. A method as set forth in claim 93 further comprising the step of creating an electrode of said needle containing said sample bearing solution.

* * * * *